US008541379B2

(12) United States Patent
Miyaki et al.

(10) Patent No.: US 8,541,379 B2
(45) Date of Patent: Sep. 24, 2013

(54) KOKUMI-IMPARTING AGENT

(75) Inventors: Takashi Miyaki, Kawasaki (JP);
Naohiro Miyamura, Kawasaki (JP);
Megumi Kaneko, Kawasaki (JP);
Yusuke Amino, Kawasaki (JP); Reiko Yasuda, Kawasaki (JP); Yuzuru Eto, Kawasaki (JP); Takaho Tajima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/529,482

(22) Filed: Jun. 21, 2012

(65) Prior Publication Data

US 2012/0277168 A1 Nov. 1, 2012

Related U.S. Application Data

(63) Continuation of application No. PCT/JP2010/073721, filed on Dec. 28, 2010.

(30) Foreign Application Priority Data

Dec. 28, 2009 (JP) .................................. 2009-297493
Oct. 6, 2010 (JP) .................................. 2010-226570

(51) Int. Cl.
*A61K 38/05* (2006.01)
*A61K 38/00* (2006.01)
*A23B 7/10* (2006.01)
*A23B 4/023* (2006.01)
*A23F 3/00* (2006.01)
*A23K 1/00* (2006.01)
*A23L 1/22* (2006.01)
*A23L 2/56* (2006.01)
*A23L 1/236* (2006.01)
*A23L 1/40* (2006.01)
*A23L 1/238* (2006.01)
*A23L 2/00* (2006.01)
*A23L 2/38* (2006.01)
*A23L 1/212* (2006.01)
*A23L 1/223* (2006.01)
*A23L 1/221* (2006.01)
*A23L 3/015* (2006.01)
*A23D 9/013* (2006.01)
*A21D 2/16* (2006.01)
*A23J 1/00* (2006.01)
*A23P 1/00* (2006.01)
*A22C 13/00* (2006.01)

(52) U.S. Cl.
USPC .......... 514/21.91; 514/1.1; 426/49; 426/531; 426/534; 426/548; 426/589; 426/590; 426/598; 426/599; 426/615; 426/638; 426/650; 426/652; 426/653; 426/654; 426/656; 426/665; 426/390

(58) Field of Classification Search
None
See application file for complete search history.

(56) References Cited

U.S. PATENT DOCUMENTS

| 8,106,020 | B2* | 1/2012 | Ohsu et al. ............... 514/21.91 |
| 8,147,892 | B2* | 4/2012 | Hofmann et al. ............ 426/534 |
| 8,173,605 | B2* | 5/2012 | Ohsu et al. ............... 514/21.91 |
| 2006/0287390 | A1 | 12/2006 | Sagawa et al. |
| 2009/0239310 | A1 | 9/2009 | Ohsu et al. |
| 2009/0246835 | A1 | 10/2009 | Iwatani et al. |
| 2010/0105864 | A1 | 4/2010 | Yoneda et al. |
| 2010/0120698 | A1* | 5/2010 | Nagasaki et al. ............... 514/18 |
| 2010/0136197 | A1* | 6/2010 | Eto et al. ...................... 426/535 |
| 2010/0183792 | A1* | 7/2010 | Nagasaki et al. ............ 426/548 |
| 2011/0046046 | A1 | 2/2011 | Hara et al. |
| 2011/0070270 | A1 | 3/2011 | Kodera et al. |
| 2011/0097805 | A1 | 4/2011 | Ohsu et al. |
| 2012/0034364 | A1 | 2/2012 | Futaki et al. |

FOREIGN PATENT DOCUMENTS

| CN | 101305281 | 11/2008 |
| JP | 2009-514791 | 4/2009 |
| WO | WO2007/055393 | 5/2007 |
| WO | WO2007/066430 | 6/2007 |
| WO | WO2008/139945 | 11/2008 |
| WO | WO2011/081185 | 7/2011 |
| WO | WO 2011129462 A2 * | 10/2011 |

OTHER PUBLICATIONS

Cobb, M. H., et al., "Structural and Conformational Properties of Peptides Interacting with the Glutathione Receptor of Hydra," Mol. Pharmacol. 1982;21(3):629-636.
Nakayama, R., et al., "Synthesis of γ-Glutamylpeptides by γ-Glutamylcysteine Synthetase from *Proteus mirabilis*," Agric. Biol. Chem. 1981;45(12):2839-2845.
Ohsu, T., et al., "Involvement of the Calcium-sensing Receptor in Human Taste Perception," J. Biol. Chem. 2010;285(2):1016-1022.
Oppenheimer, L., et al., "Glutathione Synthetase," J. Biol. Chem. 1979;254(12):5184-5190.
Toelstede, S., et al., "Kokumi-Active Glutamyl Peptides in Cheeses and Their Biogeneration by *Penicillium roquefortii*," J. Agric. Food Chem. 2009;57:3738-3748.

(Continued)

*Primary Examiner* — Marcela M Cordero Garcia
*Assistant Examiner* — Thea D'Ambrosio
(74) *Attorney, Agent, or Firm* — Shelly Guest Cermak Cermak Nakajima LLP

(57) ABSTRACT

A substance capable of imparting a kokumi having CaSR agonist activity is described. This substance is able to impart kokumi in a superior manner, in particular, at the initial taste, and is also highly stable and can easily be produced at a low cost. The present invention thus provides a kokumi-imparting composition which includes such a substance as well as a complex kokumi-imparting composition which includes the substance and other substances possessing the CaSR agonist activities in combination. More particularly, the present invention herein provides a kokumi-imparting composition including γ-Glu-Nva (L-γ-glutamyl-L-norvaline), and a complex kokumi-imparting composition including the foregoing substance and another substance having a CaSR agonist activity, in combination.

10 Claims, 1 Drawing Sheet

(56) References Cited

OTHER PUBLICATIONS

Toelstede, S., et al., "A Series of Kokumi Peptides Impart the Long-Lasting Mouthfulness of Matured Gouda Cheese," J. Agric. Food Chem. 2009;57:1440-1448.

International Search Report and Written Opinion for PCT Patent App. No. PCT/JP2010/073721 (Feb. 1, 2011).

Office Action and Search Report issued in Taiwan Patent App. No. 099146666 (May 10, 2013).

* cited by examiner

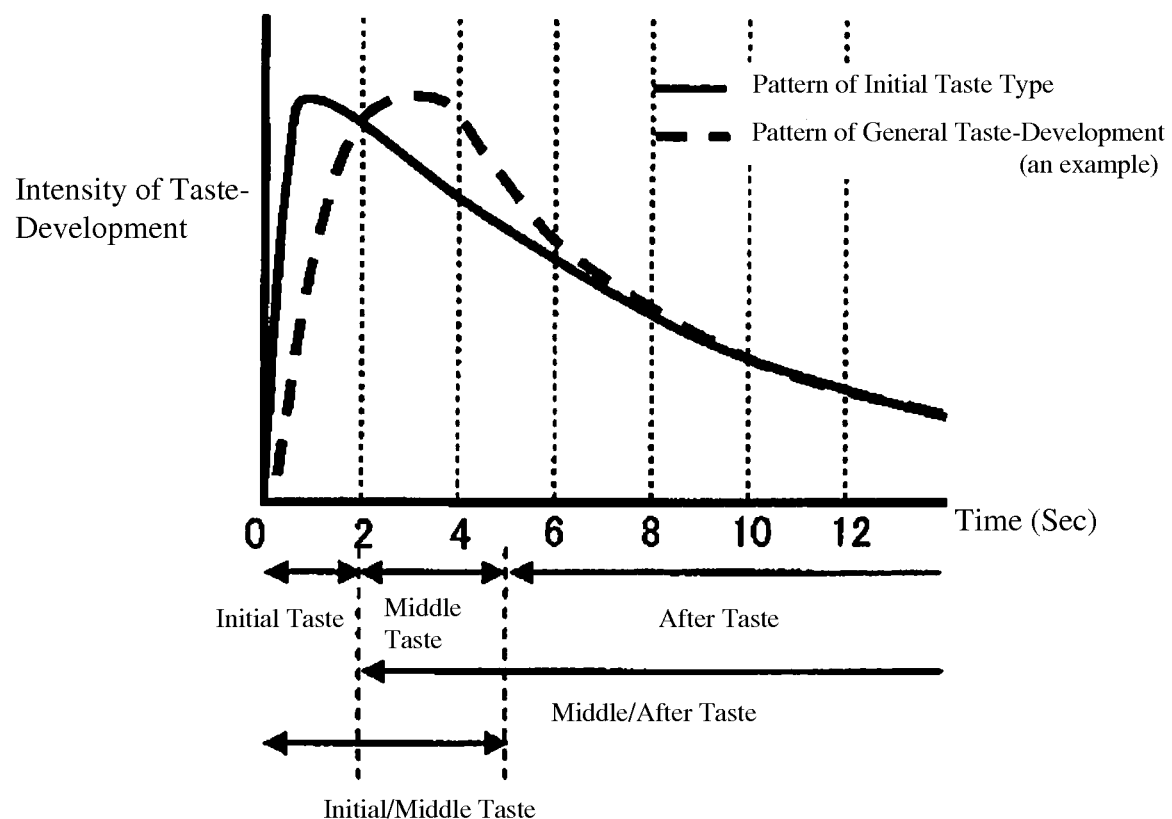

SEQUENCE LISTING

```
<160> NUMBER OF SEQ ID NOS: 4

<210> SEQ ID NO 1
<211> LENGTH: 4924
<212> TYPE: DNA
<213> ORGANISM: Homo sapiens
<220> FEATURE:
<221> NAME/KEY: CDS
<222> LOCATION: (373)..(3609)
```

-continued

<400> SEQUENCE: 1

```
caacaggcac ctggctgcag ccaggaagga ccgcacgccc tttcgcgcag gagagtggaa      60
ggagggagct gtttgccagc accgaggtct tgcggcacag gcaacgcttg acctgagtct     120
tgcagaatga aaggcatcac aggaggcctc tgcatgatgt ggcttccaaa gactcaagga     180
ccacccacat tacaagtctg gattgaggaa ggcagaaatg gagattcaaa caccacgtct     240
tctattattt tattaatcaa tctgtagaca tgtgtcccca ctgcagggag tgaactgctc     300
caagggagaa acttctggga gcctccaaac tcctagctgt ctcatccctt gccctggaga     360
gacggcagaa cc atg gca ttt tat agc tgc tgc tgg gtc ctc ttg gca ctc    411
               Met Ala Phe Tyr Ser Cys Cys Trp Val Leu Leu Ala Leu
                 1               5                  10
```

| | | |
|---|---|---|
| acc tgg cac acc tct gcc tac ggg cca gac cag cga gcc caa aag aag<br>Thr Trp His Thr Ser Ala Tyr Gly Pro Asp Gln Arg Ala Gln Lys Lys<br>  15                  20              25 | | 459 |
| ggg gac att atc ctt ggg ggg ctc ttt cct att cat ttt gga gta gca<br>Gly Asp Ile Ile Leu Gly Gly Leu Phe Pro Ile His Phe Gly Val Ala<br>30                35               40              45 | | 507 |
| gct aaa gat caa gat ctc aaa tca agg ccg gag tct gtg gaa tgt atc<br>Ala Lys Asp Gln Asp Leu Lys Ser Arg Pro Glu Ser Val Glu Cys Ile<br>             50                55              60 | | 555 |
| agg tat aat ttc cgt ggg ttt cgc tgg tta cag gct atg ata ttt gcc<br>Arg Tyr Asn Phe Arg Gly Phe Arg Trp Leu Gln Ala Met Ile Phe Ala<br>        65                  70              75 | | 603 |
| ata gag gag ata aac agc agc cca gcc ctt ctt ccc aac ttg acg ctg<br>Ile Glu Glu Ile Asn Ser Ser Pro Ala Leu Leu Pro Asn Leu Thr Leu<br>80                85               90 | | 651 |
| gga tac agg ata ttt gac act tgc aac acc gtt tct aag gcc ttg gaa<br>Gly Tyr Arg Ile Phe Asp Thr Cys Asn Thr Val Ser Lys Ala Leu Glu<br>        95                100           105 | | 699 |
| gcc acc ctg agt ttt gtt gct caa aac aaa att gat tct ttg aac ctt<br>Ala Thr Leu Ser Phe Val Ala Gln Asn Lys Ile Asp Ser Leu Asn Leu<br>110             115            120           125 | | 747 |
| gat gag ttc tgc aac tgc tca gag cac att ccc tct acg att gct gtg<br>Asp Glu Phe Cys Asn Cys Ser Glu His Ile Pro Ser Thr Ile Ala Val<br>               130            135           140 | | 795 |
| gtg gga gca act ggc tca ggc gtc tcc acg gca gtg gca aat ctg ctg<br>Val Gly Ala Thr Gly Ser Gly Val Ser Thr Ala Val Ala Asn Leu Leu<br>             145               150           155 | | 843 |
| ggg ctc ttc tac att ccc cag gtc agt tat gcc tcc tcc agc aga ctc<br>Gly Leu Phe Tyr Ile Pro Gln Val Ser Tyr Ala Ser Ser Ser Arg Leu<br>             160            165            170 | | 891 |
| ctc agc aac aag aat caa ttc aag tct ttc ctc cga acc atc ccc aat<br>Leu Ser Asn Lys Asn Gln Phe Lys Ser Phe Leu Arg Thr Ile Pro Asn<br>175                 180            185 | | 939 |
| gat gag cac cag gcc act gcc atg gca gac atc atc gag tat ttc cgc<br>Asp Glu His Gln Ala Thr Ala Met Ala Asp Ile Ile Glu Tyr Phe Arg<br>190             195            200           205 | | 987 |
| tgg aac tgg gtg ggc aca att gca gct gat gac gac tat ggg cgg ccg<br>Trp Asn Trp Val Gly Thr Ile Ala Ala Asp Asp Asp Tyr Gly Arg Pro<br>             210            215           220 | | 1035 |
| ggg att gag aaa ttc cga gag gaa gct gag gaa agg gat atc tgc atc<br>Gly Ile Glu Lys Phe Arg Glu Glu Ala Glu Glu Arg Asp Ile Cys Ile<br>             225            230           235 | | 1083 |
| gac ttc agt gaa ctc atc tcc cag tac tct gat gag gaa gag atc cag<br>Asp Phe Ser Glu Leu Ile Ser Gln Tyr Ser Asp Glu Glu Glu Ile Gln<br>             240            245           250 | | 1131 |
| cat gtg gta gag gtg att caa aat tcc acg gcc aaa gtc atc gtg gtt<br>His Val Val Glu Val Ile Gln Asn Ser Thr Ala Lys Val Ile Val Val | | 1179 |

```
                       255                 260                 265
ttc tcc agt ggc cca gat ctt gag ccc ctc atc aag gag att gtc cgg      1227
Phe Ser Ser Gly Pro Asp Leu Glu Pro Leu Ile Lys Glu Ile Val Arg
270                 275                 280                 285 cgc aat atc acg ggc aag atc tgg ctg gcc agc gag gcc tgg gcc agc      1275
Arg Asn Ile Thr Gly Lys Ile Trp Leu Ala Ser Glu Ala Trp Ala Ser
            290                 295                 300 tcc tcc ctg atc gcc atg cct cag tac ttc cac gtg gtt ggc ggc acc      1323
Ser Ser Leu Ile Ala Met Pro Gln Tyr Phe His Val Val Gly Gly Thr
        305                 310                 315 att gga ttc gct ctg aag gct ggg cag atc cca ggc ttc cgg gaa ttc      1371
Ile Gly Phe Ala Leu Lys Ala Gly Gln Ile Pro Gly Phe Arg Glu Phe
    320                 325                 330 ctg aag aag gtc cat ccc agg aag tct gtc cac aat ggt ttt gcc aag      1419
Leu Lys Lys Val His Pro Arg Lys Ser Val His Asn Gly Phe Ala Lys
335                 340                 345 gag ttt tgg gaa gaa aca ttt aac tgc cac ctc caa gaa ggt gca aaa      1467
Glu Phe Trp Glu Glu Thr Phe Asn Cys His Leu Gln Glu Gly Ala Lys
350                 355                 360                 365 gga cct tta cct gtg gac acc ttt ctg aga ggt cac gaa gaa agt ggc      1515
Gly Pro Leu Pro Val Asp Thr Phe Leu Arg Gly His Glu Glu Ser Gly
            370                 375                 380 gac agg ttt agc aac agc tcg aca gcc ttc cga ccc ctc tgt aca ggg      1563
Asp Arg Phe Ser Asn Ser Ser Thr Ala Phe Arg Pro Leu Cys Thr Gly
        385                 390                 395 gat gag aac atc agc agt gtc gag acc cct tac ata gat tac acg cat      1611
Asp Glu Asn Ile Ser Ser Val Glu Thr Pro Tyr Ile Asp Tyr Thr His
    400                 405                 410 tta cgg ata tcc tac aat gtg tac tta gca gtc tac tcc att gcc cac      1659
Leu Arg Ile Ser Tyr Asn Val Tyr Leu Ala Val Tyr Ser Ile Ala His
415                 420                 425 gcc ttg caa gat ata tat acc tgc tta cct ggg aga ggg ctc ttc acc      1707
Ala Leu Gln Asp Ile Tyr Thr Cys Leu Pro Gly Arg Gly Leu Phe Thr
430                 435                 440                 445 aat ggc tcc tgt gca gac atc aag aaa gtt gag gcg tgg cag gtc ctg      1755
Asn Gly Ser Cys Ala Asp Ile Lys Lys Val Glu Ala Trp Gln Val Leu
            450                 455                 460 aag cac cta cgg cat cta aac ttt aca aac aat atg ggg gag cag gtg      1803
Lys His Leu Arg His Leu Asn Phe Thr Asn Asn Met Gly Glu Gln Val
        465                 470                 475 acc ttt gat gag tgt ggt gac ctg gtg ggg aac tat tcc atc atc aac      1851
Thr Phe Asp Glu Cys Gly Asp Leu Val Gly Asn Tyr Ser Ile Ile Asn
    480                 485                 490 tgg cac ctc tcc cca gag gat ggc tcc atc gtg ttt aag gaa gtc ggg      1899
Trp His Leu Ser Pro Glu Asp Gly Ser Ile Val Phe Lys Glu Val Gly
495                 500                 505 tat tac aac gtc tat gcc aag aag gga gaa aga ctc ttc atc aac gag      1947
Tyr Tyr Asn Val Tyr Ala Lys Lys Gly Glu Arg Leu Phe Ile Asn Glu
510                 515                 520                 525 gag aaa atc ctg tgg agt ggg ttc tcc agg gag gtg ccc ttc tcc aac      1995
Glu Lys Ile Leu Trp Ser Gly Phe Ser Arg Glu Val Pro Phe Ser Asn
            530                 535                 540 tgc agc cga gac tgc ctg gca ggg acc agg aaa ggg atc att gag ggg      2043
Cys Ser Arg Asp Cys Leu Ala Gly Thr Arg Lys Gly Ile Ile Glu Gly
        545                 550                 555 gag ccc acc tgc tgc ttt gag tgt gtg gag tgt cct gat ggg gag tat      2091
Glu Pro Thr Cys Cys Phe Glu Cys Val Glu Cys Pro Asp Gly Glu Tyr
    560                 565                 570 agt gat gag aca gat gcc agt gcc tgt aac aag tgc cca gat gac ttc      2139
Ser Asp Glu Thr Asp Ala Ser Ala Cys Asn Lys Cys Pro Asp Asp Phe
```

|  |  |
|---|---|
| 575 580 585 | |
| tgg tcc aat gag aac cac acc tcc tgc att gcc aag gag atc gag ttt<br>Trp Ser Asn Glu Asn His Thr Ser Cys Ile Ala Lys Glu Ile Glu Phe<br>590           595           600           605 | 2187 |
| ctg tcg tgg acg gag ccc ttt ggg atc gca ctc acc ctc ttt gcc gtg<br>Leu Ser Trp Thr Glu Pro Phe Gly Ile Ala Leu Thr Leu Phe Ala Val<br>                610           615           620 | 2235 |
| ctg ggc att ttc ctg aca gcc ttt gtg ctg ggt gtg ttt atc aag ttc<br>Leu Gly Ile Phe Leu Thr Ala Phe Val Leu Gly Val Phe Ile Lys Phe<br>          625           630           635 | 2283 |
| cgc aac aca ccc att gtc aag gcc acc aac cga gag ctc tcc tac ctc<br>Arg Asn Thr Pro Ile Val Lys Ala Thr Asn Arg Glu Leu Ser Tyr Leu<br>          640           645           650 | 2331 |
| ctc ctc ttc tcc ctg ctc tgc tgc ttc tcc agc tcc ctg ttc ttc atc<br>Leu Leu Phe Ser Leu Leu Cys Cys Phe Ser Ser Ser Leu Phe Phe Ile<br>          655           660           665 | 2379 |
| ggg gag ccc cag gac tgg acg tgc cgc ctg cgc cag ccg gcc ttt ggc<br>Gly Glu Pro Gln Asp Trp Thr Cys Arg Leu Arg Gln Pro Ala Phe Gly<br>670           675           680           685 | 2427 |
| atc agc ttc gtg ctc tgc atc tca tgc atc ctg gtg aaa acc aac cgt<br>Ile Ser Phe Val Leu Cys Ile Ser Cys Ile Leu Val Lys Thr Asn Arg<br>                690           695           700 | 2475 |
| gtc ctc ctg gtg ttt gag gcc aag atc ccc acc agc ttc cac cgc aag<br>Val Leu Leu Val Phe Glu Ala Lys Ile Pro Thr Ser Phe His Arg Lys<br>          705           710           715 | 2523 |
| tgg tgg ggg ctc aac ctg cag ttc ctg ctg gtt ttc ctc tgc acc ttc<br>Trp Trp Gly Leu Asn Leu Gln Phe Leu Leu Val Phe Leu Cys Thr Phe<br>          720           725           730 | 2571 |
| atg cag att gtc atc tgt gtg atc tgg ctc tac acc gcg ccc ccc tca<br>Met Gln Ile Val Ile Cys Val Ile Trp Leu Tyr Thr Ala Pro Pro Ser<br>735           740           745 | 2619 |
| agc tac cgc aac cag gag ctg gag gat gag atc atc ttc atc acg tgc<br>Ser Tyr Arg Asn Gln Glu Leu Glu Asp Glu Ile Ile Phe Ile Thr Cys<br>750           755           760           765 | 2667 |
| cac gag ggc tcc ctc atg gcc ctg ggc ttc ctg atc ggc tac acc tgc<br>His Glu Gly Ser Leu Met Ala Leu Gly Phe Leu Ile Gly Tyr Thr Cys<br>                770           775           780 | 2715 |
| ctg ctg gct gcc atc tgc ttc ttc ttt gcc ttc aag tcc cgg aag ctg<br>Leu Leu Ala Ala Ile Cys Phe Phe Phe Ala Phe Lys Ser Arg Lys Leu<br>          785           790           795 | 2763 |
| ccg gag aac ttc aat gaa gcc aag ttc atc acc ttc agc atg ctc atc<br>Pro Glu Asn Phe Asn Glu Ala Lys Phe Ile Thr Phe Ser Met Leu Ile<br>          800           805           810 | 2811 |
| ttc ttc atc gtc tgg atc tcc ttc att cca gcc tat gcc agc acc tat<br>Phe Phe Ile Val Trp Ile Ser Phe Ile Pro Ala Tyr Ala Ser Thr Tyr<br>          815           820           825 | 2859 |
| ggc aag ttt gtc tct gcc gta gag gtg att gcc atc ctg gca gcc agc<br>Gly Lys Phe Val Ser Ala Val Glu Val Ile Ala Ile Leu Ala Ala Ser<br>830           835           840           845 | 2907 |
| ttt ggc ttg ctg gcg tgc atc ttc ttc aac aag atc tac atc att ctc<br>Phe Gly Leu Leu Ala Cys Ile Phe Phe Asn Lys Ile Tyr Ile Ile Leu<br>                850           855           860 | 2955 |
| ttc aag cca tcc cgc aac acc atc gag gag gtg cgt tgc agc acc gca<br>Phe Lys Pro Ser Arg Asn Thr Ile Glu Glu Val Arg Cys Ser Thr Ala<br>          865           870           875 | 3003 |
| gct cac gct ttc aag gtg gct gcc cgg gcc acg ctg cgc cgc agc aac<br>Ala His Ala Phe Lys Val Ala Ala Arg Ala Thr Leu Arg Arg Ser Asn<br>          880           885           890 | 3051 |
| gtc tcc cgc aag cgg tcc agc agc ctt gga ggc tcc acg gga tcc acc<br>Val Ser Arg Lys Arg Ser Ser Ser Leu Gly Gly Ser Thr Gly Ser Thr | 3099 |

```
                    895                 900                 905
ccc tcc tcc tcc atc agc agc aag agc aac agc gaa gac cca ttc cca     3147
Pro Ser Ser Ser Ile Ser Ser Lys Ser Asn Ser Glu Asp Pro Phe Pro
910                 915                 920                 925 cag ccc gag agg cag aag cag cag cag ccg ctg gcc cta acc cag caa     3195
Gln Pro Glu Arg Gln Lys Gln Gln Gln Pro Leu Ala Leu Thr Gln Gln
                930                 935                 940 gag cag cag cag cag ccc ctg acc ctc cca cag cag caa cga tct cag     3243
Glu Gln Gln Gln Gln Pro Leu Thr Leu Pro Gln Gln Gln Arg Ser Gln
            945                 950                 955 cag cag ccc aga tgc aag cag aag gtc atc ttt ggc agc ggc acg gtc     3291
Gln Gln Pro Arg Cys Lys Gln Lys Val Ile Phe Gly Ser Gly Thr Val
        960                 965                 970 acc ttc tca ctg agc ttt gat gag cct cag aag aac gcc atg gcc cac     3339
Thr Phe Ser Leu Ser Phe Asp Glu Pro Gln Lys Asn Ala Met Ala His
    975                 980                 985 agg aat tct acg cac cag aac tcc ctg gag gcc  cag aaa agc agc gat   3387
Arg Asn Ser Thr His Gln Asn Ser Leu Glu Ala  Gln Lys Ser Ser Asp
990                 995                 1000                1005 acg ctg acc cga cac  cag cca tta ctc ccg  ctg cag tgc ggg gaa       3432
Thr Leu Thr Arg His  Gln Pro Leu Leu Pro  Leu Gln Cys Gly Glu
                1010                 1015                1020 acg gac tta gat ctg  acc gtc cag gaa aca  ggt ctg caa gga cct       3477
Thr Asp Leu Asp Leu  Thr Val Gln Glu Thr  Gly Leu Gln Gly Pro
                1025                1030                1035 gtg ggt gga gac cag  cgg cca gag gtg gag  gac cct gaa gag ttg       3522
Val Gly Gly Asp Gln  Arg Pro Glu Val Glu  Asp Pro Glu Glu Leu
                1040                1045                1050 tcc cca gca ctt gta  gtg tcc agt tca cag  agc ttt gtc atc agt       3567
Ser Pro Ala Leu Val  Val Ser Ser Ser Gln  Ser Phe Val Ile Ser
                1055                1060                1065 ggt gga ggc agc act gtt aca gaa aac gta gtg aat tca taa              3609
Gly Gly Gly Ser Thr Val Thr Glu Asn Val Val Asn Ser
                1070                1075 aatggaagga gaagactggg ctagggagaa tgcagagagg tttcttgggg tcccagggaa    3669
gaggaatcgc cccagactcc tttcctctga ggaagaaggg ataatagaca catcaaatgc    3729
cccgaattta gtcacaccat cttaaatgac agtgaattga cccatgttcc ctttaaaatt    3789
aaaaaaaaga agagccttgt gtttctgtgg ttgcatttgt caaagcattg agatctccac    3849
ggtcagattt gctgttcacc cacatctaat gtctcttcct ctgttctatc ccacccaaca    3909
gctcagagat gaaactatgg ctttaaacta ccctccagag tgtgcagact gatgggacat    3969
caaatttgcc accactagag ctgagagtct gaaagacaga atgtcaccag tcctgcccaa    4029
tgccttgaca acagactgaa ttttaaatgt tcacaacata aggagaatgt atctcctcct    4089
atttatgaaa accatatgat attttgtctc ctacctgctg ctgctattat gtaacatcca    4149
gaaggtttgc acccctccta taccatatgt ctgcttctgt ccaggacatg atactgatgc    4209
catgtttaga ttccaggatc acaagaatca cctcaaattg ttaggaaggg actgcataaa    4269
ccaatgagct gtatctgtaa ttaatattcc tatatgtagc tttatcctta ggaaaatgct    4329
tctgttgtaa tagtccatgg acaatataaa ctgaaaaatg tcagtctggt ttatataagg    4389
cagtattatt gagctctatt tccccacccc actatcctca ctcccataag ctaagcctta    4449
tgtgagcccc ttcagggact caagggtcca gaagtccctc ccatctctac cccaaagaat    4509
tcctgaagcc agatccaccc tatccctgta cagagtaagt tctcaattat tggcctgcta    4569
atagctgcta gggtaggaaa gcgtggttcc aagaaagatc caccctcaaa tgtcagagct    4629
```

-continued

```
atgttccctc cagcagtggt attaatactg ccggtcaccc aggctctgga gccagagaga    4689
cagaccgggg ttcaagccat ggcttcgtca tttgcaagct gagtgactgt aggcagggaa    4749
ccttaacctc tctaagccac agcttcttca tctttaaaat aaggataata atcattcttt    4809
cccctcagag ctcttatgtg gattaaacga gataatgtat ataaagtact ttagcctggt    4869
acctagcaca caataagcat tcaataaata ttagttaata ttattaaaaa aaaaa         4924
```

<210> SEQ ID NO 2
<211> LENGTH: 1078
<212> TYPE: PRT
<213> ORGANISM: Homo sapiens

<400> SEQUENCE: 2

```
Met Ala Phe Tyr Ser Cys Cys Trp Val Leu Leu Ala Leu Thr Trp His
1               5                   10                  15

Thr Ser Ala Tyr Gly Pro Asp Gln Arg Ala Gln Lys Lys Gly Asp Ile
            20                  25                  30

Ile Leu Gly Gly Leu Phe Pro Ile His Phe Gly Val Ala Ala Lys Asp
        35                  40                  45

Gln Asp Leu Lys Ser Arg Pro Glu Ser Val Glu Cys Ile Arg Tyr Asn
    50                  55                  60

Phe Arg Gly Phe Arg Trp Leu Gln Ala Met Ile Phe Ala Ile Glu Glu
65                  70                  75                  80

Ile Asn Ser Ser Pro Ala Leu Leu Pro Asn Leu Thr Leu Gly Tyr Arg
                85                  90                  95

Ile Phe Asp Thr Cys Asn Thr Val Ser Lys Ala Leu Glu Ala Thr Leu
            100                 105                 110

Ser Phe Val Ala Gln Asn Lys Ile Asp Ser Leu Asn Leu Asp Glu Phe
        115                 120                 125

Cys Asn Cys Ser Glu His Ile Pro Ser Thr Ile Ala Val Val Gly Ala
    130                 135                 140

Thr Gly Ser Gly Val Ser Thr Ala Val Ala Asn Leu Leu Gly Leu Phe
145                 150                 155                 160

Tyr Ile Pro Gln Val Ser Tyr Ala Ser Ser Ser Arg Leu Leu Ser Asn
                165                 170                 175

Lys Asn Gln Phe Lys Ser Phe Leu Arg Thr Ile Pro Asn Asp Glu His
            180                 185                 190

Gln Ala Thr Ala Met Ala Asp Ile Ile Glu Tyr Phe Arg Trp Asn Trp
        195                 200                 205

Val Gly Thr Ile Ala Ala Asp Asp Asp Tyr Gly Arg Pro Gly Ile Glu
    210                 215                 220

Lys Phe Arg Glu Glu Ala Glu Glu Arg Asp Ile Cys Ile Asp Phe Ser
225                 230                 235                 240

Glu Leu Ile Ser Gln Tyr Ser Asp Glu Glu Ile Gln His Val Val
                245                 250                 255

Glu Val Ile Gln Asn Ser Thr Ala Lys Val Ile Val Phe Ser Ser
            260                 265                 270

Gly Pro Asp Leu Glu Pro Leu Ile Lys Glu Ile Val Arg Arg Asn Ile
        275                 280                 285

Thr Gly Lys Ile Trp Leu Ala Ser Glu Ala Trp Ala Ser Ser Ser Leu
    290                 295                 300

Ile Ala Met Pro Gln Tyr Phe His Val Val Gly Gly Thr Ile Gly Phe
305                 310                 315                 320

Ala Leu Lys Ala Gly Gln Ile Pro Gly Phe Arg Glu Phe Leu Lys Lys
                325                 330                 335
```

-continued

```
Val His Pro Arg Lys Ser Val His Asn Gly Phe Ala Lys Glu Phe Trp
            340                 345                 350

Glu Glu Thr Phe Asn Cys His Leu Gln Glu Gly Ala Lys Gly Pro Leu
            355                 360                 365

Pro Val Asp Thr Phe Leu Arg Gly His Glu Glu Ser Gly Asp Arg Phe
370                 375                 380

Ser Asn Ser Ser Thr Ala Phe Arg Pro Leu Cys Thr Gly Asp Glu Asn
385                 390                 395                 400

Ile Ser Ser Val Glu Thr Pro Tyr Ile Asp Tyr Thr His Leu Arg Ile
                405                 410                 415

Ser Tyr Asn Val Tyr Leu Ala Val Tyr Ser Ile Ala His Ala Leu Gln
                420                 425                 430

Asp Ile Tyr Thr Cys Leu Pro Gly Arg Gly Leu Phe Thr Asn Gly Ser
            435                 440                 445

Cys Ala Asp Ile Lys Lys Val Glu Ala Trp Gln Val Leu Lys His Leu
450                 455                 460

Arg His Leu Asn Phe Thr Asn Asn Met Gly Glu Gln Val Thr Phe Asp
465                 470                 475                 480

Glu Cys Gly Asp Leu Val Gly Asn Tyr Ser Ile Ile Asn Trp His Leu
                485                 490                 495

Ser Pro Glu Asp Gly Ser Ile Val Phe Lys Glu Val Gly Tyr Tyr Asn
            500                 505                 510

Val Tyr Ala Lys Lys Gly Glu Arg Leu Phe Ile Asn Glu Glu Lys Ile
            515                 520                 525

Leu Trp Ser Gly Phe Ser Arg Glu Val Pro Phe Ser Asn Cys Ser Arg
530                 535                 540

Asp Cys Leu Ala Gly Thr Arg Lys Gly Ile Ile Glu Gly Glu Pro Thr
545                 550                 555                 560

Cys Cys Phe Glu Cys Val Glu Cys Pro Asp Gly Glu Tyr Ser Asp Glu
                565                 570                 575

Thr Asp Ala Ser Ala Cys Asn Lys Cys Pro Asp Asp Phe Trp Ser Asn
            580                 585                 590

Glu Asn His Thr Ser Cys Ile Ala Lys Glu Ile Glu Phe Leu Ser Trp
            595                 600                 605

Thr Glu Pro Phe Gly Ile Ala Leu Thr Leu Phe Ala Val Leu Gly Ile
            610                 615                 620

Phe Leu Thr Ala Phe Val Leu Gly Val Phe Ile Lys Phe Arg Asn Thr
625                 630                 635                 640

Pro Ile Val Lys Ala Thr Asn Arg Glu Leu Ser Tyr Leu Leu Leu Phe
                645                 650                 655

Ser Leu Leu Cys Cys Phe Ser Ser Ser Leu Phe Phe Ile Gly Glu Pro
            660                 665                 670

Gln Asp Trp Thr Cys Arg Leu Arg Gln Pro Ala Phe Gly Ile Ser Phe
            675                 680                 685

Val Leu Cys Ile Ser Cys Ile Leu Val Lys Thr Asn Arg Val Leu Leu
            690                 695                 700

Val Phe Glu Ala Lys Ile Pro Thr Ser Phe His Arg Lys Trp Trp Gly
705                 710                 715                 720

Leu Asn Leu Gln Phe Leu Leu Val Phe Leu Cys Thr Phe Met Gln Ile
                725                 730                 735

Val Ile Cys Val Ile Trp Leu Tyr Thr Ala Pro Pro Ser Ser Tyr Arg
            740                 745                 750

Asn Gln Glu Leu Glu Asp Glu Ile Ile Phe Ile Thr Cys His Glu Gly
```

```
                    755                 760                 765
Ser Leu Met Ala Leu Gly Phe Leu Ile Gly Tyr Thr Cys Leu Leu Ala
    770                 775                 780

Ala Ile Cys Phe Phe Phe Ala Phe Lys Ser Arg Lys Leu Pro Glu Asn
785                 790                 795                 800

Phe Asn Glu Ala Lys Phe Ile Thr Phe Ser Met Leu Ile Phe Phe Ile
                805                 810                 815

Val Trp Ile Ser Phe Ile Pro Ala Tyr Ala Ser Thr Tyr Gly Lys Phe
            820                 825                 830

Val Ser Ala Val Glu Val Ile Ala Ile Leu Ala Ala Ser Phe Gly Leu
        835                 840                 845

Leu Ala Cys Ile Phe Phe Asn Lys Ile Tyr Ile Ile Leu Phe Lys Pro
    850                 855                 860

Ser Arg Asn Thr Ile Glu Glu Val Arg Cys Ser Thr Ala Ala His Ala
865                 870                 875                 880

Phe Lys Val Ala Ala Arg Ala Thr Leu Arg Arg Ser Asn Val Ser Arg
                885                 890                 895

Lys Arg Ser Ser Ser Leu Gly Gly Ser Thr Gly Ser Thr Pro Ser Ser
            900                 905                 910

Ser Ile Ser Ser Lys Ser Asn Ser Glu Asp Pro Phe Pro Gln Pro Glu
        915                 920                 925

Arg Gln Lys Gln Gln Pro Leu Ala Leu Thr Gln Glu Gln Gln
    930                 935                 940

Gln Gln Pro Leu Thr Leu Pro Gln Gln Arg Ser Gln Gln Pro
945                 950                 955                 960

Arg Cys Lys Gln Lys Val Ile Phe Gly Ser Gly Thr Val Thr Phe Ser
                965                 970                 975

Leu Ser Phe Asp Glu Pro Gln Lys Asn Ala Met Ala His Arg Asn Ser
            980                 985                 990

Thr His Gln Asn Ser Leu Glu Ala  Gln Lys Ser Ser Asp  Thr Leu Thr
        995                 1000                1005

Arg His  Gln Pro Leu Leu Pro  Leu Gln Cys Gly Glu  Thr Asp Leu
    1010                1015                1020

Asp Leu  Thr Val Gln Glu Thr  Gly Leu Gln Gly Pro  Val Gly Gly
    1025                1030                1035

Asp Gln  Arg Pro Glu Val Glu  Asp Pro Glu Glu Leu  Ser Pro Ala
    1040                1045                1050

Leu Val  Val Ser Ser Ser Gln  Ser Phe Val Ile Ser  Gly Gly Gly
    1055                1060                1065

Ser Thr  Val Thr Glu Asn Val  Val Asn Ser
    1070                1075
```

<210> SEQ ID NO 3
<211> LENGTH: 49
<212> TYPE: DNA
<213> ORGANISM: Artificial
<220> FEATURE:
<223> OTHER INFORMATION: primer

<400> SEQUENCE: 3
actaatacga ctcactatag ggaccatggc attttatagc tgctgctgg                49

<210> SEQ ID NO 4
<211> LENGTH: 29
<212> TYPE: DNA
<213> ORGANISM: Artificial
<220> FEATURE:

```
<223> OTHER INFORMATION: primer

<400> SEQUENCE: 4
ttatgaattc actacgtttt ctgtaacag                                              29
```

KOKUMI-IMPARTING AGENT

This application is a Continuation of, and claims priority under 35 U.S.C. §120 to, International Application No. PCT/JP2010/073721, filed Dec. 28, 2010, and claims priority therethrough under 35 U.S.C. §119 to Japanese Patent Application No. 2009-297493, filed Dec. 28, 2009, and Japanese Patent Application No. 2010-226570, filed Oct. 6, 2010, the entireties of which are incorporated by reference herein. Also, the Sequence Listing filed electronically herewith is hereby incorporated by reference (File name: 2012-06-21T_US-483_Seq_List; File size: 27 KB; Date recorded: Jun. 21, 2012).

BACKGROUND OF THE INVENTION

1. Field of the Invention

The present invention relates to a kokumi-imparting agent and composition, which includes a peptide showing a CaSR agonist activity. Moreover, the present invention also relates to a food, beverage, and/or seasoning composition which includes a peptide showing a CaSR agonist activity in a concentration of not less than a predetermined level.

2. Description of the Related Art

Consumers' demands on the taste and palatability of foods have recently increased due to, for instance, the diversity of human eating habits. The taste and palatability of a food have conventionally been expressed by the five basic tastes: sweet, salty, sour, bitter and umami. However, at the same time, the development of an agent or composition capable of imparting "kokumi" to a food has been desired. Kokumi means a taste that cannot be expressed by the five basic tastes, and also includes marginal tastes of the basic tastes, such as thickness, growth (or mouthfullness), continuity, and harmony.

The calcium sensing receptor (CaSR) can also be referred to as the calcium receptor, and the signals from the receptor control a variety of biological functions within living bodies. Substances with CaSR agonist activity can be used as a kokumi-imparting agent (see International Patent Laid-Open No. 2007/055393, Pamphlet; International Patent Laid-Open No. 2008/139945, Pamphlet; and The Journal of Biological Chemistry, (2010), 285 (2), 1016-22).

There are a variety of taste-developing patterns for describing "kokumi". In this respect, there has been an intensive need, in particular, for the development of a kokumi-imparting agent capable of imparting the kokumi to a food, and such agent have a taste-developing pattern of kokumi whose profile is an initial taste type. Moreover, the agent or composition for imparting kokumi can, in general, be used in, for instance, foods and accordingly, it should be highly stable. In addition, the agent or composition for imparting the kokumi should be able easily produced at a low cost from the industrial standpoint.

Accordingly, much research has been conducted on a variety of compounds possessing the desired CaSR agonist activity with the goal of isolating a substance or agent capable of imparting kokumi to other substances, such as foods and beverages, in a superior manner. In particular, the substance or agent should possess a kokumi-imparting effect whose profile is the initial taste-imparting type, be highly stable, and be easily produced at a low cost. Such a kokumi-imparting agent or substance can be used alone, or as an ingredient in a more complex composition which can include the substance and other substances possessing the CaSR agonist activities in combination.

γ-Glutamyl peptides having a γ-glutamine residue at the N-terminal thereof have been reported as being used as synthesized substrates in, for instance, research of enzymatic activities (International Patent Laid-Open No. 2007/066430, Pamphlet; Molecular Pharmacology (1982), 21(3), 629-36; Agricultural and Biological Chemistry (1981), 45(12), 2839-45; and Journal of Biological Chemistry (1979), 254(12), 5184-90). However, there have been no reports to date of the use of γ-Glu-Nva in food, or that it even exists in nature.

SUMMARY OF THE INVENTION

It is an aspect of the present invention to describe a variety of compounds possessing CaSR agonist activity which are capable of imparting kokumi, and which possess an excellent kokumi-imparting effect. In particular, the described compounds possess a kokumi-imparting effect as the initial taste (type one), which is highly stable and which can easily be produced at a low cost. Furthermore, it is an aspect to provide a composition which contains such a substance as well as other substances possessing the CaSR agonist activities in combination. It is a further aspect of the present invention to provide a food, beverage, and/or seasoning composition which contains the foregoing substance in a concentration of not less than the predetermined level.

It has been found that γ-Glu-Nva (L-γ-glutamyl-L-norvaline) possesses a high CaSR agonist activity and a quite excellent kokumi-imparting effect. In particular, this substance possesses a taste-developing (or flavoring) pattern that permits the impartment of kokumi as the initial taste to a subject. Furthermore, it has been found that γ-Glu-Nva has an extremely high titer, is highly stable, and has such a favorable taste-developing pattern that it shows a strong initial taste, as compared with those observed for γ-Glu-Cys. Moreover, it has been found that γ-Glu-Nva can serve as a useful kokumi-imparting agent by itself. Moreover, it has likewise been found that a food composition with improved kokumi can be obtained by the incorporation of γ-Glu-Nva into the food. In addition, a complex kokumi-imparting composition can be obtained by combining the substance with other substances having CaSR agonist activity.

It is an aspect of the present invention to provide a kokumi-imparting agent consisting of γ-Glu-Nva.

It is a further aspect of the present invention to provide a food composition comprising γ-Glu-Nva.

It is a further aspect of the present invention to provide a complex kokumi-imparting composition which comprises (a) γ-Glu-Nva and (b) a substance selected from the group consisting of γ-Glu-X-Gly wherein X represents an amino acid or an amino acid derivative, γ-Glu-Val-Y wherein Y represents an amino acid or an amino acid derivative, γ-Glu-Abu, γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met (O), γ-Glu-γ-Glu-Val, γ-Glu-Val-NH$_2$, γ-Glu-Val-ol, γ-Glu-Ser, γ-Glu-Tau, γ-Glu-Cys (S-Me) (O), γ-Glu-Leu, γ-Glu-Ile, γ-Glu-t-Leu, γ-Glu-Cys (S-Me), and combinations thereof.

It is a further aspect of the present invention to provide a food composition comprising γ-Glu-Nva in an amount ranging from 0.1 ppb to 99.9% by mass.

It is a further aspect of the present invention to provide the food composition as described above, comprising 0.005 to 30 ppm by mass of γ-Glu-Nva; 0.01 to 10% by mass of herbs and/or spices derived from the plants belonging to Labiatae; and any other food ingredients.

It is a further aspect of the present invention to provide the food composition as described above, comprising 0.02 to 80 ppm by mass of γ-Glu-Nva; 0.01 to 99.9% by mass of miso; and any other food ingredients.

It is a further aspect of the present invention to provide the food composition as described above, comprising: a) 0.02 to 80 ppm by mass of γ-Glu-Nva; and b) 0.01 to 99.9% by mass of tomato.

It is a further aspect of the present invention to provide a method for preparing a food or beverage, or an intermediate used for preparing a food or beverage comprising the steps of: A) adding a flavor enhancer consisting essentially of γ-Glu-Nva to food ingredients, B) mixing them together; and C) optionally cooking the resulting mixture.

It is a further aspect of the present invention to provide the method as described above, wherein said adding the flavor enhancer consisting essentially of γ-Glu-Nva to food ingredients comprises controlling the concentration of γ-Glu-Nva in the intermediate used for preparing a food or beverage to a level ranging from 0.005 to 600,000 ppm by mass.

It is a further aspect of the present invention to provide the method as described above, wherein the method further comprises the step of adding an intermediate for preparing a food or beverage to other food ingredients while controlling the concentration of γ-Glu-Nva in the resulting food or beverage to a level ranging from 0.005 to 30 ppm by mass.

It is a further aspect of the present invention to provide the method as described above, wherein said adding the flavor enhancer consisting essentially of γ-Glu-Nva to the food ingredients, and said mixing them together, comprises the step of controlling the concentration of γ-Glu-Nva in the resulting food or beverage to a level of from 0.005 to 30 ppm by mass.

It is a further aspect of the present invention to provide the method as described above, wherein the food or beverage is a food comprising an herb and/or spice derived from a plant belonging to Labiatae.

It is a further aspect of the present invention to provide the method as described above, wherein the food or beverage comprising miso.

It is a further aspect of the present invention to provide the method as described above, wherein the food or beverage comprises tomato.

It is a further aspect of the present invention to provide a food or beverage, or an intermediate used for preparing a food or beverage, characterized in that it is prepared according to the method as described above.

It is a further aspect of the present invention to provide a method for enhancing the flavor and/or taste of a food or beverage, comprising the step of adding a composition comprising γ-Glu-Nva to a food or beverage.

It is a further aspect of the present invention to provide the method as described above, wherein the flavor and/or taste-enhancing step is a kokumi-imparting step.

The present invention provides a kokumi-imparting agent which is quite excellent in its kokumi-imparting effect and, in particular, has an excellent and unique kokumi-imparting effect at the initial taste, as shown in, for instance, FIG. 1. The agent or composition containing the agent also is highly stable and can easily be prepared at a low cost. In addition, the present invention provides an excellent food composition which comprises a substance possessing an excellent kokumi-imparting effect in a concentration of not less than a predetermined level.

The kokumi-imparting agent or composition has a flavor and/or taste-developing pattern quite similar to that observed for common salt and therefore, when using the kokumi-imparting agent or composition, a salty taste-like thick impression and an initial taste-punch (or impact) can be imparted to the low salt food. Accordingly, the resulting low salt food containing the agent or composition can maintain a salty taste similar to its taste profile prior to the reduction of the salt content, and therefore, the agent or composition permits the production of a food which is highly beneficial to health. Examples of such foods include a variety of soups and various kinds of sauces. Especially, if eating a food containing the kokumi-imparting agent according to the present invention, the consumer can feel the salty taste-like thick impression and an initial taste-punch (or impact) immediately after eating the same.

BRIEF DESCRIPTION OF THE DRAWINGS

FIG. 1 shows the taste-developing profile for a kokumi-imparting agent of the initial taste (type one).

DESCRIPTION OF THE PREFERRED EMBODIMENTS

The substance, γ-Glu-Nva, described herein, also referred to as L-γ-glutamyl-L-norvaline, contains two amino acids that are linked to one another through a peptide bond and/or salts thereof, in particular, edible salts thereof.

The substance, γ-Glu-Nva, shows an excellent kokumi-imparting effect and therefore, it can be used as a kokumi-imparting agent. γ-Glu-Nva can be used in a food composition to which the kokumi is to be imparted, wherein the dipeptide is present in the food composition in an amount (the range of the concentration) ranging from 0.1 ppb by mass to 99.9% by mass, 1 ppb by mass to 10% by mass, or 0.01 ppm by mass to 1% by mass relative to the total mass of the food composition. In other words, a food composition is described which contains γ-Glu-Nva in an amount ranging from 0.1 ppb by mass to 99.9% by mass, 1 ppb by mass to 10% by mass, or even 0.01 ppm by mass to 1% by mass. More specifically, a food composition is described containing γ-Glu-Nva in an amount of not less than 0.1 ppb by mass, not less than 0.005 ppm by mass, not less than 0.02 ppm by mass, or not less than 0.01% by mass, to not more than 99.9% by mass, not more than 90.0% by mass, not more than 50% by mass, not more than 600,000 ppm by mass, not more than 100,000 ppm by mass, not more than 80 ppm by mass, not more than 30 ppm by mass, or not more than 10 ppm by mass, as expressed in terms of the mass thereof.

Moreover, the kokumi-imparting agent or γ-Glu-Nva can also be used in combination with at least one additional seasoning ingredient such as, for example, amino acids such as sodium glutamate (MSG), nucleic acids such as inosine monophosphate (IMP), inorganic salts such as sodium chloride, organic acids such as citric acid, and various kinds of yeast extracts to thus provide a favorable seasoning composition which contributes to the improvement in kokumi, as compared with that obtained by the use of such additional seasoning ingredients individually. When using γ-Glu-Nva in combination with the foregoing additional seasoning ingredients, the concentration of the former can easily or properly be determined or established by one of ordinary skill in the art after conducting investigations, for instance, the sensory test.

The term "kokumi" can mean a taste which cannot be expressed by the five basic tastes, which are sweet, salty, sour, bitter and umami, and more specifically means the marginal taste of the basic tastes, such as thickness, growth (mouthfullness), continuity, and harmony, in which such marginal tastes are enhanced in addition to the basic tastes. In addition, the term "kokumi-imparting" can mean that the five basic tastes are enhanced, while the marginal tastes of the basic tastes associated with the former are simultaneously imparted to a subject. Moreover, this can also be referred to as a flavor-enhancing effect. Therefore, the γ-Glu-Nva serving as the kokumi-imparting agent of the present invention can likewise be referred to as a "flavor enhancer". The kokumi-imparting agent or γ-Glu-Nva may also be used as a sweet taste enhancer, a salty taste enhancer, a sour taste enhancer, a bitter taste enhancer, or an umami enhancer.

Moreover, the taste of a food may vary over time. In general, the tastes once the food has been placed in the mouth, and then as time passes, can be referred to as the initial taste, the middle taste, and the after taste, in order, starting immediately after placing the food in the mouth. Although this is a relative concept, the initial taste, the middle taste, and the after taste are, as a whole, defined as the tastes observed from 0 to 2 seconds, 2 to 5 seconds, and not less than 5 seconds after eating the food, respectively. The taste observed during the term extending from 0 to 5 seconds can be referred to as the "initial/middle taste" and that observed during the term extending from 2 to about 30 seconds can be referred to as the "middle/after taste" (see the data plotted on FIG. 1). When the taste is divided into three subdivisions, it can be difficult for the panelists (persons who eat and evaluate the food) to concentrate their attention on the evaluation, and so the commonly used test includes the evaluation of the taste while dividing it into two subdivisions.

Moreover, the combined initial taste and middle taste is referred to as the "initial/middle taste" and the combined middle taste and after taste is referred to as the "middle/after taste".

The effects of a substance with CaSR activity on the kokumi and the taste-developing pattern can be confirmed by a method, for instance, a human sensory test for the evaluation of taste. An example of such a human sensory test for the evaluation of taste is illustrated in Examples, but any sensory test for the evaluation of taste known in the art can be used, and is not restricted to this specific one.

The term "CaSR" can mean the calcium sensing receptor which belongs to the class C of the 7-transmembrane receptors, and which is thus also referred to as "calcium receptor". The term "CaSR agonist" can mean a substance which binds to the foregoing CaSR to thus activate the CaSR receptor. In addition, the phrase "activate CaSR" can mean that a ligand is bound with the CaSR to thus activate a protein linked with a guanine nucleotide and to transmit signals outputted from the same. Moreover, the ability of a substance to form a bond with CaSR to thus activate the same is referred to as "CaSR agonist activity".

Although not limited to the following steps and/or methods, a method for screening a compound having a CaSR agonist activity can be as follows:

1) Adding a test substance to a CaSR activity-measuring system to determine the CaSR activity;

2) Comparing the CaSR activity observed in step (1) with that observed in the same system prior to the addition of the substance; and 3) Selecting a substance which has CaSR agonist activity when it is added to the CaSR activity-measuring system.

The determination of the CaSR activity can likewise be carried out while using, for instance, a measuring system that uses cells having an ability of expressing CaSR. The foregoing cells can endogeneously express the CaSR, or can be cells into which a gene expressing the CaSR is exogeneously introduced. The aforementioned CaSR activity-measuring system is not restricted to any specific one inasmuch as it can permit the detection of the bond or reaction between the CaSR-activation substance and CaSR, or it can emit or output a detectable signal in response to the formation of the bond or reaction between the CaSR-activation substance and CaSR within the cells, when adding an extracellular ligand (activating substance) specific to CaSR to the foregoing cells having an ability of expressing CaSR. If the CaSR activity is detected through the reaction with a test substance, then the test substance can be deemed as having the desired CaSR-stimulation activity.

An example of the foregoing CaSR can be human CaSR encoded by the human CaSR gene registered under the GenBank Accession Number of NM_000388. In this respect, however, the CaSR is not restricted to the protein encoded by the gene having the foregoing sequence of the registered CaSR, and it can be any protein capable of being encoded by the gene having not less than 60%, not less than 80%, or not less than 90% of the sequence homology with the foregoing gene sequence, inasmuch as the protein encoded by such a gene can possess the desired CaSR function. In this connection, the CaSR function can be examined by expressing these genes in cells and then determining any change of an electric current and/or any change in the calcium ion concentration within the cells observed when calcium is added to a system containing the cells.

The source of foregoing CaSR is not restricted, and the CaSR can be derived from animals including mice, rats and canines, in addition to the foregoing human CaSR.

As has been discussed above, the CaSR activity can be confirmed through the use of cells capable of expressing the CaSR or a fragment thereof, cell membranes which can express CaSR or a fragment thereof, or an in vitro system including the CaSR or a protein as a fragment thereof.

An example using such cells is given below, but the present invention is by no means limited to this example.

CaSR can be expressed in cultured cells such as oocytes of *xenopus*, ovarian cells derived from hamsters, and/or human fetal renal cells. CaSR expression can be carried out by introducing, into a plasmid possessing an exogenous gene, the CaSR gene which has been subjected to the cloning treatment in the form of a plasmid or cRNA obtained using the same as a template. The reaction can be detected by measuring an increase in the calcium concentration within the cells by electrophysiological means or a fluorescent indicator.

The expression of CaSR can be initially confirmed by the observation of a response when adding calcium or an activator having specificity thereto. More specifically, cells can be used in which an intracellular electric current is detected upon adding calcium in a concentration of about 5 mM, or when fluorescent rays are emitted upon the addition of a fluorescent indicator. In this connection, the concentration of calcium added to the cells can be variously changed to determine any calcium concentration-dependency of the intensity of the intracellular electric current. Then, a test substance can be diluted to a concentration ranging from about 1 μM to 1 mM, the resulting dispersion can be added to oocytes or cultivated cells, and the CaSR activity in the presence of the foregoing test substance can be measured to thus determine the CaSR agonist activity of the test substance.

More specifically, a test for the determination of the CaSR agonist activity can be, for instance, the test illustrated in the Test Examples herein, but the activity-determining test is not limited to such a specific one.

The amino acids or peptides used in the kokumi-imparting composition in combination with γ-Glu-Nva can include, for instance, one or at least two of the following amino acids or peptides: γ-Glu-X-Gly (wherein X represents an amino acid or an amino acid derivative), γ-Glu-Val-Y (wherein Y represents an amino acid or an amino acid derivative), γ-Glu-Abu, γ-Glu-Ala, γ-Glu-Gly, γ-Glu-Cys, γ-Glu-Met, γ-Glu-Thr, γ-Glu-Val, γ-Glu-Orn, Asp-Gly, Cys-Gly, Cys-Met, Glu-Cys, Gly-Cys, Leu-Asp, D-Cys, γ-Glu-Met (O), γ-Glu-γ-Glu-Val, γ-Glu-Val-NH$_2$, γ-Glu-Val-ol, γ-Glu-Ser, γ-Glu-Tau, γ-Glu-Cys (S-Me) (O), γ-Glu-Leu, γ-Glu-Ile, γ-Glu-t-Leu and γ-Glu-Cys (S-Me). In this respect, the amino acids can likewise include, for instance, neutral amino acids such as Gly, Ala, Val, Leu, Be, Ser, Thr, Cys, Met, Asn, Gln, Pro, Hyp, t-Leu; acidic amino acids such as Asp, Glu; basic amino acids such as Lys, Arg, His; aromatic amino acids such as Phe, Tyr, Trp; as well as homoserine, citrulline, ornithine, α-aminobutyric acid, norvaline, norleucine, and taurine. Moreover, the amino acids can be artificial amino acids having non-proteinaceous construction such as tert-leucine, cyclo-leucine, α-aminoiso-butyric acid, L-penicillamine, allothreonine, and allo-isoleucine. In this connection, in the peptide γ-Glu-X-Gly, X can be the aforementioned amino acid or derivative thereof, but can also be an amino acid or derivatives thereof other than Cys. The following are particular examples: γ-Glu-Val-Gly, γ-Glu-Abu-Gly, γ-Glu-tLeu-Gly, γ-Glu-Nva-Gly and γ-Glu-Abu.

In particular, the kokumi-imparting agent or composition can be γ-Glu-Nva, and have a unique and excellent kokumi-imparting effect at the initial taste, whose taste-developing (flavoring) profile is as shown in FIG. 1. γ-Glu-Nva can be used in combination with a peptide such as γ-Glu-Val-Gly, which shows a taste-developing profile different from that of the former.

Each amino acid residue can be expressed using the following abbreviations:
(1) Gly: glycine;
(2) Ala: alanine;
(3) Val: valine;
(4) Leu: leucine;
(5) Ile: isoleucine;
(6) Met: methionine;
(7) Phe: phenylalanine;
(8) Tyr: tyrosine;
(9) Trp: tryptophane;
(10) His: histidine;
(11) Lys: lysine;
(12) Arg: arginine;
(13) Ser: serine;
(14) Thr: threonine;
(15) Asp: aspartic acid;
(16) Glu: glutamic acid;
(17) Asn: asparagine;
(18) Gln: glutamine;
(19) Cys: cysteine;
(20) Pro: proline;
(21) Orn: ornithine;
(22) Sar: sarcosine;
(23) Cit: citrulline;
(24) N-Val: (or Nva): norvaline (2-aminovaleric acid);
(25) N-Leu (or Nle): norleucine;
(26) Abu: α-aminobutyric acid;
(27) Tau: taurine;
(28) Hyp: hydroxy-proline;
(29) t-Leu: tert-leucine;
(30) Cle: cyclo-leucine;
(31) Aib: α-amino-isobutyric acid (2-methyl-alanine);
(32) Pen: L-penicillamine;
(33) allo-Thr: allothreonine;
(34) allo-Ile: allo-isoleucine.

Furthermore, the term "amino acid derivative" can mean a variety of derivatives of the foregoing amino acids, and specific examples include special amino acids and artificial amino acids, amino alcohols, or amino acids whose side chains of amino acids such as terminal carboxyl groups, amino groups and/or thiol group of cysteine are substituted with a variety of substituents. Examples of such substituents can include an alkyl group, an acyl group, a hydroxyl group, an amino group, an alkylamino group, a nitro group, a sulfonyl group, or a variety of protective groups. Thus, examples of such amino acid derivatives include Arg (NO$_2$): N-γ-nitroalginine, Cys (SNO): S-nitro-cysteine, Cys (S-Me): S-methyl cysteine, Cys (5-allyl): 5-allyl cysteine, Val-NH$_2$: valine-amide, and Val-ol: valinol (2-amino-3-methyl-1-butanol). The peptide γ-Glu-Cys(SNO)-Gly can be represented by the following structural formula (Chemical Formula 1), and the symbol "(O)" appearing in the foregoing formulas γ-Glu-Met (O) and γ-Glu-Cys (S-Me) (O) can mean that these peptides each have a sulfoxide structure. The symbol "(γ)" of γ-Glu means that another amino acid is linked with the glutamic acid through the carboxyl group situating at the γ-position of the latter.

Chemical Formula 1:

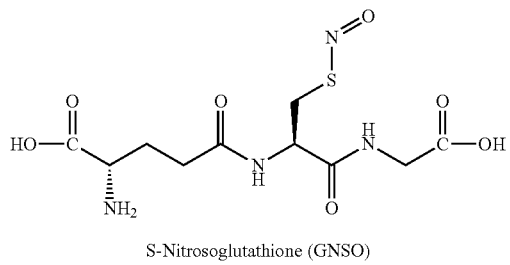

S-Nitrosoglutathione (GNSO)

The γ-Glu-Nva and the amino acids and peptides used in combination can be commercially available if they can be purchased on the market, or can be obtained according to any known technique such as (1) chemical synthetic methods or (2) a method which makes use of an enzyme reaction, but it is usually more convenient to use a chemical synthetic technique. The γ-Glu-Nva is very short in its length since it includes only two amino acid residues and therefore, it is more convenient to use a chemical synthetic technique. More specifically, it can be produced simply and at a low cost as compared with any tripeptide of three amino acid residues and accordingly, the use of this dipeptide is quite advantageous from the industrial standpoint. In addition, when chemically synthesizing the γ-Glu-Nva and the amino acids and peptides used in combination therewith, the preparation thereof may be carried out by synthesizing or semi-synthesizing these oligo-peptides while using a peptide-synthesis device. A method for chemically synthesizing these peptides can include, for instance, the solid-phase peptide-synthesis technique. The peptide thus produced can subsequently be purified according to usual techniques, such as ion-exchange chromatography, reversed phase high performance liquid chromatography, or affinity chromatography. Such a solid phase peptide-synthesis technique and the subsequently used peptide-purification technique are well known in the field of this art.

Alternatively, when producing the γ-Glu-Nva and the amino acids and peptides used in combination therewith, while making use of an enzyme reaction, the preparation thereof can be carried out by the use of the method disclosed in the pamphlet of International Patent Laid-Open WO 2004/011653. More specifically, they can be prepared by reacting an amino acid or a peptide, in which one of the terminal carboxyl group thereof is esterified or aminated, with another amino acid whose amino group is in its free state, for instance, an amino acid whose carboxyl group is protected, in the presence of a peptide-forming enzyme and then purifying the resulting dipeptide or tripeptide. Examples of such peptide-forming enzyme compositions can be cultures of microorganisms showing the ability to produce a peptide, the cell bodies of microorganisms isolated from the culture, or a product obtained by processing the cell bodies of the microorganisms, or a peptide-forming enzyme originated from the microorganisms.

In addition to the foregoing enzymatic production methods and chemical synthesis methods, the peptides can be isolated from naturally occurring products, for instance, plants such as vegetables and fruits, microorganisms such as yeast and other natural resources. When they are isolated from naturally occurring substances, the resulting isolated products can likewise be used as described herein.

The kokumi-imparting agent or composition can be used as a seasoning without any particular post-treatment or can be mixed with carriers acceptable for foods and beverages or ingredients for other seasonings to thus give various seasonings. Examples of such other ingredients for seasonings include spices, saccharides, sweeteners, edible fibers, vitamins, amino acids such as sodium glutamate (MSG), nucleic acids such as inosine monophosphate (IMP), inorganic salts such as sodium chloride, and organic acids such as citric acid as well as various kinds of yeast extracts.

Low salt foods which include the kokumi-imparting agent or composition can be, by nature, those containing common salt and, in particular, foods with reduced common salt content.

Examples of such low salt foods can include dairy products such as butter and cheese; animal oils and fats-containing and/or vegetable oils and fats-containing foods such as margarine, sauces and roux; emulsified foods such as dressings and mayonnaise; various kinds of curry and stew; and a variety of soups containing meat extracts or essences of meat and/or cream. Moreover, such low salt foods can likewise include, for instance, fermented or brewed foods such as miso and soy sauce; processed vegetable foods such as salted vegetables and pickles; meat-processed products such as hams and sausage; processed marine products such as boiled fish paste, dried marine products and foods boiled down in soy; cooked meat balls, hamburger steak; fried foods; and grilled chicken. Particular examples of low salt foods can be those having a common salt concentration, upon eating the same, ranging from 0.01 to 0.5% by mass.

If the kokumi-imparting agent or composition is incorporated into the foregoing low salt foods, the foods will be able to give, to the consumer, a salty taste-like thick impression and an initial taste-punch or impact at the initial stage, upon eating these low salt foods.

In addition, herbs and spices derived from the plants belonging to Labiatae (mint family) or foods to which these herbs and spices are added, can likewise be food compositions to which the kokumi-imparting agent or composition can be added. Examples of herbs derived from the plants belonging to Labiatae include anis, oregano, sage, thyme, Japanese mint, peppermint, bergamot, marjoram, mint, lavender and rosemary in addition to beefsteak plant and basil, but they are not restricted to these specific ones at all. In case of the foods containing such herbs and/or spices derived from the plants belonging to Labiatae and the kokumi-imparting agent or composition, the foregoing foods can contain the herbs and/or spices in an amount ranging from 0.01 to 10% by mass as expressed in terms of the solid content thereof, observed upon eating the same.

Examples of such foods each containing γ-Glu-Nva and the herbs and/or spices derived from the plants belonging to Labiatae include sauces, dressings, soups, snack foods or meat-processed products (such as hams and sausage).

Moreover, foods containing miso can also be used as the food composition containing the kokumi-imparting agent or composition. Examples of such miso include those prepared using malted rice, malt (malted barley) and malted soybeans as well as blended miso obtained by blending at least two of them, but the present invention is not restricted to these specific ones. Such foods containing miso are not restricted to particular ones, inasmuch as they can contain miso, but also can include, for instance, miso soups, various kinds of processed foods which comprise miso as a seasoning, seasoned miso, miso-containing soups for Chinese noodles and miso-containing sauces. In case of foods which contain miso and the kokumi-imparting agent or composition, particular examples include the foregoing miso-containing foods in which the miso or the like is present in an amount ranging from 0.01 to 99.9% by mass as expressed in terms of the solid content thereof, upon eating the same.

Furthermore, tomato-containing foods can be used as the food compositions containing the kokumi-imparting agent or composition. Such tomato-containing foods are not restricted to specific ones inasmuch as they can contain tomato, but specific examples thereof can include tomato sauces, tomato catsups, tomato pastes, and a variety of tomato-containing soups. In case of foods containing tomato and the kokumi-imparting agent or composition, the foregoing tomato-containing foods can contain tomato or the like in an amount ranging from 0.01 to 99.9% by mass as expressed in terms of the solid content thereof, observed when eating the same.

The γ-Glu-Nva and the amino acids or peptides used in combination therewith may likewise include those in their salt form. If the γ-Glu-Nva and the amino acids or peptides used in combination therewith are present in their salt form, the salts are not restricted to specific ones insomuch as they can be pharmacologically acceptable and soluble ones, and specific examples thereof can include ammonium salts, salts with alkali metals such as sodium and potassium, salts with alkaline earth metals such as calcium and magnesium, aluminum salts, zinc salts, salts with organic amines such as triethylamine, ethanolamine, morpholine, pyrrolidine, piperidine, piperazine and dicyclo-hexylamine, and salts with basic amino acids such as alginine and lysine, for the acidic groups such as carboxyl groups. Moreover, examples of the foregoing compounds likewise can include salts with inorganic acids such as hydrochloric acid, sulfuric acid, phosphoric acid, nitric acid and hydrobromic acid; salts with organic acids such as acetic acid, citric acid, benzoic acid, maleic acid, fumaric acid, tartaric acid, succinic acid, tannic acid, butyric acid, hibenzoic acid, pamoic acid, enanthic acid, decanoic acid, theoclic acid, salicylic acid, lactic acid, oxalic acid, mandelic acid and malic acid; and salts with organic sulfonic acids such as methanesulfonic acid, benzenesulfonic acid and p-toluenesulfonic acid, for the basic groups of the compounds.

The kokumi-imparting agent or composition, or the food composition can be used in any form, including dried powders, pastes, and solutions, without any restriction in the physical properties thereof.

The kokumi-imparting agent or composition, or the food composition can be incorporated into, for instance, a variety of foods, beverages, and seasonings.

When incorporating the kokumi-imparting agent or composition, or the food composition into, for instance, foods, beverages, and seasonings, the ultimate amount of γ-Glu-Nva and/or one or more amino acids and/or peptides, the amount is not restricted to any specific amount inasmuch as the desired kokumi-imparting effects of the agent or composition are achieved, but the amount of γ-Glu-Nva and/or that of the amino acid or peptide each fall within the range of from about 0.1 ppb by mass to 99.9% by mass, about 1 ppb by mass to 10% by mass, or about 0.01 ppm by mass to 1% by mass on the basis of the total mass of each corresponding food, beverage, seasoning or the like.

A variety of foods, beverages or seasonings can be used to incorporate the incorporated kokumi-imparting agent or composition, or food composition, and can further include, for instance, any solid or liquid carrier and/or appropriate seasoning ingredients, which are acceptable for foods and beverages.

As the foregoing carriers, there can be listed, for instance, glucose, lactose, saccharose, starch, mannitol, dextrin, fatty acid glycerides, polyethylene glycol, hydroxyethyl starch, ethylene glycol, polyoxyethylene sorbitan fatty acid esters, gelatine, albumin, amino acids, water, and physiological saline.

The aforementioned ingredients for seasonings are not restricted to any particular one and they may be any ones currently used in this field, but specific examples thereof are those already described above.

The contents of the foregoing carriers, other seasoning ingredients or the like are not restricted to specific ones.

Among the foregoing seasoning ingredients, the yeast extract is not particularly restricted in any of the cell bodies of microorganisms, from which the extract is originated, the conditions of cultivating the microorganisms and the methods for the extraction thereof and accordingly, any yeast extract can be used in the products. Furthermore, these yeast extracts can be ones that are subjected to, for instance, a heat-treatment, a treatment with an enzyme, a concentration treatment and/or a treatment for converting the same into powder.

The kokumi-imparting agent or composition, or the food composition can be used in any form such as dried powders, pastes, and solutions, without any restriction in the physical properties thereof.

The kokumi-imparting agent or composition, or the food composition can be incorporated into, for instance, a variety of foods, beverages and seasonings.

A method for the preparation of a variety of foods and beverages is also described, which can include the step of adding γ-Glu-Nva to a variety of intermediates used for the production of various kinds of foods and beverages, in such a manner that the resulting foods and beverages contain γ-Glu-Nva in an amount ranging from 1 ppb by mass to 99.9% by mass. In this respect, the various kinds of foods and beverages can be low salt foods.

A method is also provided for the preparation of a variety of foods or beverages, which can include the step of incorporating the food composition into intermediates used for preparing various kinds of foods or beverages. In this connection, the various kinds of foods or beverages can be low salt foods.

Regarding the method for preparing an intermediate used for preparing other foods or beverages, the method can include the steps of adding a flavor enhancer such as γ-Glu-Nva to a food ingredient, such as an umami-imparting ingredient, hydrolyzates of proteins, or herbs and/or spices, while admixing them together and, depending on necessity, further cooking the resulting mixture of the food ingredients to thus form foods or beverages or intermediates for preparing the same.

In this respect, the step of adding the flavor enhancer such as γ-Glu-Nva to the food ingredient can include the step of controlling the concentration of γ-Glu-Nva in the intermediate used for preparing a food or beverage to a level ranging from 0.005 to 600,000 ppm by mass, or 0.1 to 100,000 ppm by mass.

In addition, the method can further include the step of adding an intermediate for preparing foods or beverages to other food ingredients, such as agricultural products, marine products, livestock products, dairy products, or processed products thereof, while controlling the concentration of γ-Glu-Nva in the resulting foods or beverages to a level of from 0.005 to 30 ppm by mass, or 0.05 to 10 ppm by mass.

Moreover, the step of adding the flavor enhancer such as γ-Glu-Nva to the food ingredient, while mixing them together can include the step of controlling the concentration of γ-Glu-Nva in the resulting foods or beverages to a level of from 0.005 to 30 ppm by mass, or 0.05 to 10 ppm by mass.

In the foregoing production method, the foods or beverages can include herbs and/or spices derived from the plants belonging to Labiatae (such as sauces, dressings, soups, snack foods or meat-processed products). In this case, each food or beverage can include 0.005 to 30 ppm by mass of γ-Glu-Nva, 0.01 to 10% by mass of the herbs and/or spices derived from the plants belonging to Labiatae; and other food ingredients.

Moreover, in the foregoing production method, the food or beverage can include miso. In this case, each food or beverage can include 0.02 to 80 ppm by mass of γ-Glu-Nva, 0.01 to 99.9% by mass, or 0.1 to 90.0% by mass, of miso, and other food ingredients.

Furthermore, in the foregoing production method, the food or beverage can include tomato. In this case, each food or beverage can include 0.02 to 80 ppm by mass of γ-Glu-Nva, 0.01 to 99.9% by mass, or 0.1 to 90.0% by mass, of tomato, and other food ingredients.

Moreover, a method for enhancing flavor of foods or beverages is described, which can include the step of adding a composition containing γ-Glu-Nva to foods or beverages in an amount ranging from 0.01 to 50% by mass. In this connection, the flavor-enhancing can be a kokumi-imparting step.

The present invention will hereunder be described in more detail with reference to the following non-limiting.

EXAMPLES

Synthetic Example 1

Synthesis of γ-Glu-Nva (γ-L-glutamyl-L-norvaline)

Boc-Nva.DCHA (t-butoxycarbonyl-L-norvaline dicyclohexyl-ammonium salt, 3.39 g, 8.49 mM) and benzyl alcohol (1.01 g, 9.34 mM) were dissolved in methylene chloride ($CH_2Cl_2$, 60 mL). Then, DMAP (4-dimethylaminopyridine, 0.21 g, 0.2 eq., 1.70 mM) and WSC.HCl (1-ethyl-3-(3-dimethylaminopropyl)-carbodiimide hydrochloride, 1.81 g, 1.1 eq., 9.34 mM) were added to the resulting solution, maintained at 0° C. The temperature of the reaction solution was gradually increased and stirred at room temperature overnight (16 hours). Then the reaction solution was concentrated under reduced pressure, ethyl acetate (500 mL) was added to the resulting residue, and temperature of the organic phase was increased to 50° C. It was then washed with water (100 mL), twice with a 5% aqueous solution of citric acid (100 mL), once with a saturated common salt solution (100 mL), twice with a 5% aqueous solution of sodium hydrogen carbonate (100 mL), and once with a saturated common salt solution (100 mL), and then the organic phase was dried over anhydrous magnesium sulfate. The magnesium sulfate was removed through filtration and the filtrate was concentrated under reduced pressure. Crystals were precipitated during concentration under reduced pressure and therefore, the crystals were collected through filtration followed by drying under reduced pressure to give crystals of Boc-Nva-OBzl (2.41 g, 7.83 mM).

To Boc-Nva-OBzl combined with separately synthesized Boc-Nva-OBzl (2.68 g, 8.72 mM), a 4N HCl/dioxane solution (43.6 mL) was added, and the mixture was stirred at room temperature for one hour. The reaction system was concentrated under reduced pressure to remove the dioxane, n-hexane (30 mL) was added to the resulting residue, and then the resulting mixture was concentrated under reduced pressure. In this respect, the latter two steps were repeated three times to thus obtain H-Nva-OBzl.HCl in a quantitative yield.

The resulting H-Nva-OBzl.HCl was dissolved in methylene chloride (60 mL) and the resulting reaction solution was maintained at 0° C. To the reaction solution, Z-Glu-OBzl (N-α-carbobenzoxy-L-glutamic acid α-benzyl ester, 3.24 g, 8.72 mM), triethylamine (1.34 mL, 1.1 eq., 9.59 mM), HOBt.H$_2$O (1-hydroxybenzotriazole hydrate, 1.47 g, 1.1 eq., 9.59 mM) and WSC.HCl (1.84 g, 1.1 eq., 9.59 mM) were added. The temperature of the reaction solution was gradually increased and stirred at room temperature overnight (16 hours). Then the reaction solution was concentrated under reduced pressure, ethyl acetate (200 mL) was added to the resulting residue, and the organic phase was then washed once with water (80 mL), twice with a 5% aqueous solution of citric acid (80 mL), once with a saturated common salt solution (80 mL), twice with a 5% aqueous solution of sodium hydrogen carbonate (80 mL), and once with a saturated common salt solution (80 mL). Then, the organic phase was dried over anhydrous magnesium sulfate. The magnesium sulfate was removed through filtration and the filtrate was concentrated under reduced pressure. The resulting residue was recrystallized from ethyl acetate and n-hexane, the crystals thus obtained were collected through filtration and dried under reduced pressure to give crystals of Z-Glu(Nva-OBzl)-OBzl (4.05 g).

To a mixed solution of ethanol (150 mL) and water (30 mL), Z-Glu(Nva-OBzl)-OBzl (4.05 g) and 5% palladium on carbon (5% palladium/carbon, 0.70 g) was added, and a catalytic reducing reaction was carried out at 50° C. overnight (14 hours) in a hydrogen gas atmosphere. Water (50 mL) was added to the reaction system in small portions during the reaction. The palladium/carbon was removed from the reaction system through filtration and the resulting filtrate was concentrated under reduced pressure. The residue was recrystallized from a small amount of water and ethanol to thus give γ-Glu-Nva (1.50 g) as white crystals. Furthermore, the crystals were dissolved in water (100 mL) followed by the lyophilization of the solution to give γ-Glu-Nva (1.27 g, 5.16 mM) as white powder. The characteristic values thereof are given below:

ESI-MS: (M+H)$^+$=247.1; (M−H)$^−$=245.2.

$^1$H-NMR (400 MHz, D$_2$O): δ (ppm): 0.77 (3H, t, J=7.3 Hz), 1.18-1.33 (2H, m), 1.50-1.73 (2H, m), 1.97-2.08 (2H, m), 2.36 (2H, dd, J=0.6 and 8.4 Hz), 3.68 (1H, t, J=8.4 Hz), 4.15 (1H, dd, J=5.2 and 8.8 Hz).

Synthetic Example 2

Synthesis of γ-Glu-Nle (γ-L-glutamyl-L-norleucine) (Comparative Example)

Boc-Nle.0.2AcOEt (t-butoxycarbonyl-L-norleucine.0.2M ethyl acetate, 0.51 g, 2.00 mM) and benzyl alcohol (0.24 g, 2.22 mmol) were dissolved in methylene chloride (CH$_2$Cl$_2$, 30 mL). Then, DMAP (4-dimethylaminopyridine, 0.05 g, 0.2 eq., 0.40 mM) and WSC.HCl (1-ethyl-3-(3-dimethylaminopropyl)-carbodiimide hydrochloride, 0.43 g, 1.1 eq., 2.20 mM) were added to the resulting solution maintained at 0° C. The temperature of the reaction solution was gradually raised and stirred at room temperature overnight (16 hours). Then, the reaction solution was concentrated under reduced pressure, ethyl acetate (100 mL) was added to the resulting residue, the organic liquid was then washed once with water (30 mL), twice with a 5% aqueous solution of citric acid (30 mL), once with a saturated common salt solution (30 mL), twice with a 5% aqueous solution of sodium hydrogen carbonate (30 mL), and then once with a saturated common salt solution (30 mL). Then, the organic phase was dried over anhydrous magnesium sulfate. The magnesium sulfate was removed through filtration and the filtrate was concentrated under reduced pressure to thus give Boc-Nle-OBzl (0.61 g, 1.90 mM) as an oily product.

4N HCl/dioxane solution (9.40 mL) was added to Boc-Nle-OBzl (0.61 g, 1.90 mM), and the mixture was stirred at room temperature for one hour. The reaction system was concentrated under reduced pressure to remove the dioxane, n-hexane (5.0 mL) was added to the resulting residue, and then the resulting mixture was concentrated under reduced pressure. In this connection, the latter two steps were repeated three times to thus obtain H-Nle-OBzl.HCl in a quantitative yield.

The resulting H-Nle-OBzl.HCl was dissolved in methylene chloride (30 mL) and the resulting reaction solution was maintained at 0° C. To the reaction solution, Z-Glu-OBzl (N-α-carbobenzoxy-L-glutamic acid α-benzyl ester, 0.70 g, 1.90 mM), triethylamine (0.29 mL, 1.1 eq., 2.10 mM), HOBt.H$_2$O (1-hydroxybenzotriazole hydrate, 0.32 g, 1.1 eq., 2.10 mM), and WSC.HCl (0.41 g, 1.1 eq., 2.10 mM) was added. The temperature of the reaction solution was gradually raised and stirred at room temperature overnight (16 hours). Then, the reaction mixture was concentrated under reduced pressure, ethyl acetate (100 mL) was added to the resulting residue, and the organic phase was then washed once with water (30 mL), twice with a 5% aqueous solution of citric acid (30 mL), once with a saturated common salt solution (30 mL), twice with a 5% aqueous solution of sodium hydrogen carbonate (30 mL) and once with a saturated common salt solution (30 mL). Then, the organic phase was dried over anhydrous magnesium sulfate. The magnesium sulfate was removed through filtration and the filtrate was concentrated under reduced pressure. The resulting residue was recrystallized from ethyl acetate and n-hexane, the crystals thus obtained were collected through filtration and dried under reduced pressure to give crystals of Z-Glu(Nle-OBzl)-OBzl (0.91 g).

Z-Glu(Nle-OBzl)-OBzl (4.05 g) and 5% palladium on carbon (5% palladium/carbon, 0.40 g) were added to a mixed solution of ethanol (50 mL) and water (10 mL), and a catalytic reducing reaction was carried out at 50° C. overnight (14 hours) in a hydrogen gas atmosphere. Water (10 mL) was added to the reaction system in small portions during the reaction. The palladium/carbon was removed from the reaction system through filtration and the resulting filtrate was concentrated under reduced pressure. The residue was recrystallized from a small amount of water and ethanol to thus give γ-Glu-Nle (0.29 g) as hygroscopic crystals. Furthermore, the crystals were dissolved in water (30 mL) followed by the lyophilization of the solution to give γ-Glu-Nle (0.13 g, 0.50 mM) as a white powder. The characteristic values thereof will be given below:

ESI-MS: (M+H)$^+$=261.1; (M−H)$^−$=259.0.

$^1$H-NMR (400 MHz, D$_2$O): δ (ppm): 0.79 (3H, t, J=7.1 Hz), 1.18-1.30 (4H, m), 1.60-1.70 (1H, m), 1.70-1.80 (1H, m), 2.04-2.10 (2H, m), 2.38-2.44 (2H, m), 3.73 (1H, t, J=6.3 Hz), 4.19 (1H, dd, J=5.0 and 8.8 Hz).

Test Example 1

Preparation of CaSR-Expression Plasmid

A CaSR-expression plasmid was prepared according to the following procedures:

Synthetic oligo DNAs were synthesized and used for PCR (i.e., forward primer (ACTAATACGACTCACTATAGG-GACCATGGCA-TTTTATAGCTGCTGCTGG (SEQ ID NO: 3)) and reverse primer (TTATGAATT-CAC-TACGTTTTCTGTAACAG (SEQ ID NO: 4)) on the basis of the DNA sequence registered at NCBI (CaSR (calcium receptor): NM_000388, SEQ ID NOS: 1 and 2).

The PCR procedures were carried out under the conditions specified below using cDNA (available from Clontech Company) derived from human kidney as a template, while using the foregoing primers and Pfu Ultra DNA Polymerase (available from Stratagene Company): The reaction system was processed at 94° C. for 3 minutes, and then at 94° C. for 30 seconds, at 55° C. for 30 seconds and at 72° C. for 2 minutes, wherein these steps were repeated over 35 times and the system was finally reacted at 72° C. for 7 minutes. The reaction system was then subjected to electrophoresis treatment through agarose as a support, the agarose was stained with a DNA-staining agent and then it was irradiated with UV light rays to detect whether the cDNA was amplified by the PCR procedures or not. At the same time, the electrophoresis pattern was compared with a DNA marker of known electrophoretic size to thus confirm the chain lengths of the PCR products.

Plasmid vector pBR322 was cleaved with the restriction enzyme EcoRV (available from Takara Co., Ltd), and the gene fragment amplified by the PCR procedures was ligated with the plasmid vector at the cleaved site, using Ligation Kit (available from Promega Company). The cells of *Escherichia coli* DH5α strain were transformed with this reaction solution, followed by the selection of the transformants containing the plasmid in which the PCR-amplified product had been cloned and further the PCR-amplified product was confirmed by the DNA-base sequence analysis.

This recombinant plasmid was used for the establishment of a human CaSR-expression plasmid hCaSR/pcDNA3.1.

Test Example 2

Evaluation of CaSR Agonist Activity

293E Cells (EBNA1-expresion HEK293 cells, ATCC No. CRL-10852) were cultivated in DMEN/Ham's-F12 (3.15/mL glucose-containing Dulbecco's modified Eagle medium, available from Nakaraitesk Company) supplemented with 10% fetal calf serum, in the presence of 200 μg/mL of G418 (available from Genetisin). The cultured cells were inoculated in F25 flask at a density of $3 \times 10^6$ cells/10 mL, the flask was allowed to stand over 24 hours in a $CO_2$ incubator (5% $CO_2$, 37° C.), and then the human CaSR-expression plasmid hCaSR/pcDNA3.1 was transformed or transfected with a reagent for transfection Fugene6 (available from Roche Company). The transfected plasmid was maintained in a $CO_2$ incubator for 6 to 7 hours, then the cells were recovered using a 10% fetal calf serum-containing DMEM/Ham's-F12 and the cells were inoculated in each well of a poly-D-lysine coat 96-well plate (BD-Biocoat) at a density of 70,000 cells/well.

The 96-well plate was allowed to stand over 24 hours in a $CO_2$ incubator, then the culture medium was removed from each well of the 96-well plate in which the cells were inoculated, followed by the addition, to each well, of a $Ca^{2+}$ fluorescent indicator Calcium 4 Assay Kit (available from Molecular Devices Company) dissolved in Assay Buffer (containing 146 mM of NaCl, 5 mM of KCl, 1 mM of $MgSO_4$, 1 mg/mL of glucose, 20 mM of HEPES (pH 7.2) and 0.75 to 1.25 mM of $CaCl_2$) in an amount of 200 μl/well, and subsequently allowing the 96-well plate to stand at 37° C. for one hour and then at room temperature for 10 minutes so that the indicator was incorporated into the cells.

To each well of the 96-well plate, each test compound was dissolved in a 0.1% BSA-containing Assay Buffer in an amount of 50 μl/well, and then any change of the intensity of fluorescence was monitored over 3 minutes using FLEX Station (available from Molecular Devices Company).

Method for the Determination of $EC_{50}$:

The difference (RFU (Max-Min)) between the maximum and minimum fluorescent intensities observed for each well before and after the addition of each specific test compound was determined by the automatic calculation using FLEX Station. The activity rate was calculated while the RFU (Max-Min) value observed when adding the compound at the maximum concentration was defined to be 100% and the RFU (Max-Min) value observed when using the 0.1% BSA-containing Assay Buffer free of any test compound was defined to be 0%, followed by subjecting the resulting data to the curve-fitting procedures using the spreadsheet software Xfit or Graph-Pad-Prism to thus determine the $EC_{50}$ which was the concentration of the compound at the activity rate of 50%. The results thus obtained are summarized in the following Table 1.

In addition, the same $EC_{50}$-determining procedures used above were repeated except for using other dipeptides as Comparative Examples. The results thus obtained are summarized in the following Table 2.

TABLE 1

| Compound | $EC_{50}$, μM |
|---|---|
| γ-Glu-Nva | 0.12 |
| γ-Glu-Nle | 4.41 |

TABLE 2

| Compound | $EC_{50}$, μM |
|---|---|
| γ-Glu-Abu | 0.21 |
| γ-Glu-Ala | 1.24 |
| γ-Glu-Val | 1.03 |
| γ-Glu-tLeu | 3.06 |
| γ-Glu-Cys | 0.16 |
| γ-Glu-Ser | 11 |
| γ-Glu-Thr | 6.97 |
| γ-Glu-Aib | 15.4 |

When comparing with other dipeptides, γ-Glu-Nva was found to have a strong CaSR agonist activity comparable to that observed for γ-Glu-Cys. It was reported that a low molecular weight peptide possessing a CaSR agonist activity is useful as a kokumi-imparting agent (International Patent Laid-Open No. 2007/055393, Pamphlet) and accordingly, γ-Glu-Nva may be able to serve as a particularly excellent kokumi-imparting agent.

Example 1

Evaluation of Kokumi-Imparting Activity

In this example, γ-Glu-Nva was inspected for the intensity of its kokumi-imparting activity according to a quantitative sensory evaluation test.

This quantitative sensory evaluation test was carried out according to the following procedures: The intensity of the kokumi-imparting activity observed for each test compound was determined as a value observed when blending 0.00001 to 0.5 g/dL of the corresponding test compound with the distilled water containing sodium glutamate (0.05 g/dL), inosinic acid monophosphate (0.05 g/dL), and sodium chloride (0.5 g/dL). In this connection, when a sample showed an acidic nature upon the dissolution of the test compound as compared with the test compound-free control, the pH value of the sample was adjusted, using NaOH, to a level of the pH value (observed for the control)±0.2 prior to the practical use of the sample in the evaluation. The evaluation criteria are assumed to be as follows: control: 0 point; strong: 3 points; very strong: 5 points. Moreover, to clarify the criteria, the initial taste and the middle/after taste of γ-Glu-Val-Gly were set at 3.0 points, respectively. The scoring or rating was carried out using the method of line scale and more specifically, it was carried out by writing each corresponding score on a straight line on which points corresponding to −5~0~5 had been indicated. The panelists used in this test were defined to be persons who had been engaged in the development of seasonings for foods over not less than one year of the cumulative time period and who could judge that the difference in the titer between γ-Glu-Cys-Gly and γ-Glu-Val-Gly added to a solution having umami/salty taste is about 10 times (while confirming the ability of these persons at regular intervals). The evaluation was carried out at n (the number of panelists used)=4. The term "initial taste" means the taste which develops from 0 to 2 seconds after the sample is placed in the panelist's mouth, while the term "middle/after taste" means the taste which develops thereafter. The test compound widely showed the kokumi-imparting activity over the foregoing range of concentration thereof added. However, the results observed for typical concentrations thereof are summarized in the following Table 3.

In addition, γ-Glu-Val-Gly, γ-Glu-Cys, γ-Glu-Val, γ-Glu-Ala and γ-Glu-Ser were likewise inspected for their kokumi-imparting effect according to the same procedures used above. The results obtained are also listed in Table 3.

TABLE 3

| Compound | Conc. (g/dL) | Intensity of kokumi | | Sensory Evaluation Profile |
| --- | --- | --- | --- | --- |
| | | Initial Taste | Middle/After Taste | |
| Control | — | 0 | 0 | — |
| γ-Glu-Val-Gly | 0.001 | 3.0 | 3.0 | Mainly, the mellowness, the dense-feeling, and the growth were enhanced. |
| γ-Glu-Nva | 0.0001 | 3.6 | 2.8 | Mainly the initial and middle tastes were enhanced. |
| γ-Glu-Cys | 0.01 | 3.1 | 3.1 | Mainly the middle and after tastes were enhanced and the sample gave out a slight odor of sulfur. |
| γ-Glu-Val | 0.01 | 3.1 | 2.4 | The after taste was quite weak. |
| γ-Glu-Ala | 0.2 | 4.5 | 4.3 | Mainly the tastes similar to the sour and sweet tastes were enhanced on and after the initial taste stage. |
| γ-Glu-Ser | 0.2 | 3.6 | 3.0 | The initial taste was strong, but off-flavor were recognized. |

Thus, it was found that γ-Glu-Nva possesses an excellent kokumi-imparting activity and that it is also excellent in the development of the initial taste with respect to the seasoning pattern. This excellent development of the initial taste observed for γ-Glu-Nva is an extreme advantage as compared with that observed for γ-Glu-Cys. Moreover, γ-Glu-Nva is also excellent in its stability and this is also an advantageous point as compared with γ-Glu-Cys. Regarding the kokumi-imparting activity, γ-Glu-Nva has a high titer superior to those of the conventionally known dipeptides. In addition, γ-Glu-Nva has a short chain length since it has only two amino acid residues. Accordingly, it can be prepared relatively easily at a low cost as compared with the preparation of a tripeptide of 3 amino acid residues and accordingly, is likewise quite advantageous from the industrial standpoint.

Example 2

Effect of γ-Glu-Nva on Basil

γ-Glu-Nva is an initial taste type dipeptide. However, it was found that when eating the dipeptide, it expressed its kokumi-imparting effect and action slightly later as compared with the conventionally known initial taste type dipeptide showing high titers such as γ-Glu-Abu and γ-Glu-Val. On the other hand, it was also found that if comparing this dipeptide with the conventional middle/after taste type tripeptides such as γ-Glu-Cys-Gly (glutathione) and γ-Glu-Val-Gly, the dipeptide could quite immediately express the kokumi-imparting effect. Therefore, the inventors searched for herbs and/or spices which may be synchronized with the time at which γ-Glu-Nva can express its kokumi-imparting effect and activity to thus enhance the taste of the former and the inventors have investigated them in detail. In this connection, such characteristics have not been recognized by other γ-Glu peptides having high kokumi-imparting effect and activity.

More specifically, the sensory evaluation test was carried out according to the following procedures: Commercially available typical herb/spice in powdery form was dispersed in water in a concentration of 0.5% by mass to thus form a herb/spice solution. This solution was admixed with γ-Glu-Nva, γ-Glu-Cys-Gly, or γ-Glu-Abu as a test compound. According to the paired comparison test, the panelists were requested to comparatively evaluate the following three samples and to judge whether "any of them was preferred since it could enhance the flavor and taste of the herb/spice solution without changing the balance between them": (1) 0.02% by mass of γ-Glu-Cys-Gly whose kokumi-imparting activity was identical to 0.00015% by mass of γ-Glu-Nva; (2) 0.00015% by mass of γ-Glu-Abu, the amount of which was identical to 0.00015% by mass of γ-Glu-Nva; (3) 0.003% by mass of γ-Glu-Abu whose kokumi-imparting activity was identical to that observed for 0.00015% by mass of γ-Glu-Nva. The panelists used in this test were persons who had been engaged in the development of seasonings for foods over not less than one year of the cumulative time period and who could judge that the difference in the titer between γ-Glu-Cys-Gly and γ-Glu-Val-Gly added to a solution having umami/salty taste is about 10 times (while confirming the ability of these persons at regular intervals). The evaluation was carried out at N (the number of panelists used)=9.

The following Table 4 shows the number of panelists who judged that 0.00015% by mass of γ-Glu-Nva was "rather preferred since it could enhance the flavor and taste of the herb/spice solution without changing the balance between them". The herbs and/or spices derived from the plants belonging to Labiatae certainly showed the desired effects, but the results observed for basil are shown as the typical example thereof.

From the results thus obtained, it could be concluded as follows: γ-Glu-Nva shows such a remarkable effect that it can significantly and extremely enhance the flavor and taste of the herbs and/or spices derived from the plants belonging to Labiatae even in cases where the titers of the kokumi are identical to one another like the cases of (1) and (3).

TABLE 4

| Sample | Conc. (wt %) | Sample | Conc. (wt %) | No. of Panelists* |
|---|---|---|---|---|
| (1) γ-Glu-Nva | 0.00015 | γ-Glu-Cys-Gly | 0.02 | 9/9** |
| (2) γ-Glu-Nva | 0.00015 | γ-Glu-Abu | 0.00015 | 9/9** |
| (3) γ-Glu-Nva | 0.00015 | γ-Glu-Abu | 0.003 | 8/9*** |

N = 9
*The number of panelists who judged that γ-Glu-Nva was rather preferred since it could enhance the flavor and taste of the solution of basil belonging to Labiatae, without changing the balance between them.
**The result indicates that γ-Glu-Nva is rather preferred since it can enhance the flavor and taste of the solution of basil belonging to Labiatae, without changing the balance between them, at a significant level of 1%.
***The result indicates that γ-Glu-Nva is rather preferred since it can enhance the flavor and taste of the solution of basil belonging to Labiatae, without changing the balance between them, at a significant level of 5%.

The foregoing results clearly indicate that γ-Glu-Nva shows the following quite remarkable effect: it can "enhance and make more favorable the flavor and taste of herbs and/or spices derived from the plants belonging to Labiatae without changing the balance between them", when comparing them with those observed for γGlu peptides having high kokumi-imparting activities such as γ-Glu-Cys-Gly and γ-Glu-Abu at concentrations capable of exhibiting the same kokumi-imparting activities. Examples of the herbs and/or spices derived from the plants belonging to Labiatae include a variety of plants, in addition to beefsteak plant and basil, anis, oregano, sage, thyme, Japanese mint, peppermint, bergamot, marjoram, mint, lavender and rosemary. These herbs and/or spices are widely used throughout the world in, for instance, seasonings, soups, sauces, processed meat products, cooked and processed products and confectionery, including Italian meals. As has been discussed above, γ-Glu-Nva would permit the improvement of the flavor and taste of foods which make use of herbs and/or spices derived from the plants belonging to Labiatae, at a low cost, while using the same only in a trace amount and therefore, the use thereof is quite advantageous from the industrial standpoint.

Example 3

Effect of γ-Glu-Nva on Miso

γ-Glu-Nva is an initial taste type dipeptide. However, it was found that when eating the dipeptide, it expressed its kokumi-imparting effect and action, slightly later as compared with other known initial taste type dipeptide showing high titers such as γ-Glu-Abu and γ-Glu-Val. On the other hand, it was also found that if comparing this dipeptide with the conventional middle/after taste type tripeptides such as γ-Glu-Cys-Gly (glutathione) and γ-Glu-Val-Gly, the dipeptide could quite immediately express the kokumi-imparting effect. The inventors searched for seasonings or the like which may be synchronized with the time at which γ-Glu-Nva can express its kokumi-imparting effect and activity to thus enhance the taste of the former and the inventors have investigated them in detail. In this connection, such characteristics have not been recognized by other γ-Glu peptides having high kokumi-imparting effect and activity.

More specifically, the sensory evaluation test was carried out according to the following procedures: Commercially available miso (ingredients: soybeans and barley) for popular use was dispersed in hot water in a concentration of 10.0% by mass to thus form a solution of miso. This solution was admixed with γ-Glu-Nva, γ-Glu-Cys-Gly, or γ-Glu-Abu as a test compound. According to the paired comparison test method (pair test), the panelists were requested to comparatively evaluate the following three samples and to judge whether "any of them was preferred or favorable since it could enhance the flavor and taste of the solution of miso without changing the balance between them": (1) 0.02% by mass of γ-Glu-Cys-Gly whose kokumi-imparting activity was identical to 0.0004% by mass of γ-Glu-Nva; (2) 0.0004% by mass of γ-Glu-Abu, the amount of which was identical to 0.0004% by mass of γ-Glu-Nva; (3) 0.003% by mass of γ-Glu-Abu whose kokumi-imparting activity was identical to that observed for 0.0004% by mass of γ-Glu-Nva. The panelists used in this test were persons who had been engaged in the development of seasonings for foods over not less than one year of the cumulative time period and who could judge that the difference in the titer between γ-Glu-Cys-Gly and γ-Glu-Val-Gly added to a solution having umami/salty taste is about 10 times (while confirming the ability of these persons at regular intervals). The evaluation was carried out at N (the number of panelists used)=9.

The following Table 5 shows the number of panelists who judged that 0.0004% by mass of γ-Glu-Nva was "rather preferred since it could enhance the flavor and taste of the solution of miso without changing the balance between them".

From the results thus obtained, it could be concluded as follows: γ-Glu-Nva shows such a remarkable effect that it can significantly and extremely enhance the flavor and taste of the miso even in cases where the titers of the kokumi were identical to one another like the cases of (1) and (3).

TABLE 5

| Sample | Conc. (wt %) | Sample | Conc. (wt %) | No. of Panelists* |
|---|---|---|---|---|
| (1) γ-Glu-Nva | 0.0004 | γ-Glu-Cys-Gly | 0.02 | 8/9** |
| (2) γ-Glu-Nva | 0.0004 | γ-Glu-Abu | 0.0004 | 9/9*** |
| (3) γ-Glu-Nva | 0.0004 | γ-Glu-Abu | 0.003 | 9/9*** |

N = 9
*The number of panelists who judged that γ-Glu-Nva was rather preferred since it could enhance the flavor and taste of the solution of miso, without changing the balance between them.
**The result indicates that γ-Glu-Nva is rather preferred since it can enhance the flavor and taste of the solution of miso, without changing the balance between them, at a significant level of 5%.
***The result indicates that γ-Glu-Nva is rather preferred since it can enhance the flavor and taste of the solution of miso, without changing the balance between them, at a significant level of 1%.

The foregoing results clearly indicate that γ-Glu-Nva shows the following quite remarkable effect: it can "enhance and make, more favorable, the flavor and taste of miso without changing the balance between them", when comparing them with those observed for γGlu peptides having high kokumi-imparting activities such as γ-Glu-Cys-Gly and γ-Glu-Abu, at concentrations capable of exhibiting the same kokumi-imparting activities. Miso has widely been used in, for instance, seasonings, soup or broth, sauces and cooked and processed products. As has been discussed above, γ-Glu-Nva would permit the improvement of the flavor and taste of foods which make use of miso, at a low cost, while using the same only in a trace amount and therefore, the use thereof is quite advantageous from the industrial standpoint.

Example 4

Effect of γ-Glu-Nva on Tomato Catsup

γ-Glu-Nva is an initial taste type dipeptide. However, it was found that when eating this dipeptide, it expressed its kokumi-imparting effect and action, slightly later as compared with other known initial taste type dipeptide showing high titers such as γ-Glu-Abu and γ-Glu-Val. On the other hand, it was also found that if comparing this dipeptide with the conventional middle/after taste type tripeptides such as γ-Glu-Cys-Gly (glutathione) and γ-Glu-Val-Gly, the dipeptide could quite immediately express the kokumi-imparting effect. The inventors searched for seasonings or the like which may be synchronized with the time at which γ-Glu-Nva can express its kokumi-imparting effect and activity to thus enhance the taste of the former and the inventors have investigated them in detail. In this connection, such characteristics have not been recognized by other γ-Glu peptides having high kokumi-imparting effect and activity.

More specifically, the sensory evaluation test was carried out according to the following procedures: Commercially available tomato catsup for popular use was dispersed in hot water in a concentration of 33.3% by mass to thus form a solution of tomato catsup. This solution was admixed with γ-Glu-Nva, γ-Glu-Cys-Gly, or γ-Glu-Abu as a test compound. According to the paired comparison test method (pair test), the panelists were requested to comparatively evaluate the following three samples and to judge whether "any of them was preferred or favorable since it could enhance the flavor and taste of the solution of tomato catsup without changing the balance between them": (1) 0.02% by mass of γ-Glu-Cys-Gly whose kokumi-imparting activity was identical to 0.0004% by mass of γ-Glu-Nva; (2) 0.0004% by mass of γ-Glu-Abu, the amount of which was identical to 0.0004% by mass of γ-Glu-Nva; (3) 0.003% by mass of γ-Glu-Abu whose kokumi-imparting activity was identical to that observed for 0.0004% by mass of γ-Glu-Nva. The panelists used in this test were persons who had been engaged in the development of seasonings for foods over not less than one year of the cumulative time period and who could judge that the difference in the titer between γ-Glu-Cys-Gly and γ-Glu-Val-Gly added to a solution having umami/salty taste was about 10 times (while confirming the ability of these persons at regular intervals). The evaluation was carried out at N (the number of panelists used)=9.

The following Table 6 shows the number of panelists who judged that 0.0004% by mass of γ-Glu-Nva was "rather preferred or favorable since it could enhance the flavor and taste of the solution of tomato catsup without changing the balance between them". Other sauces or the like comprising tomato as an ingredient certainly showed the desired effects. However, the results observed for tomato catsup are shown in Table 6 as the typical example thereof.

From the results thus obtained, it could be concluded as follows: γ-Glu-Nva shows such a remarkable effect that it can significantly and extremely enhance the flavor and taste of the tomato even in cases where the titers of the kokumi were identical to one another like the cases of (1) and (3).

TABLE 6

| Sample | Conc. (wt %) | Sample | Conc. (wt %) | No. of Panelists* |
| --- | --- | --- | --- | --- |
| (1) γ-Glu-Nva | 0.0004 | γ-Glu-Cys-Gly | 0.02 | 9/9** |
| (2) γ-Glu-Nva | 0.0004 | γ-Glu-Abu | 0.0004 | 9/9** |
| (3) γ-Glu-Nva | 0.0004 | γ-Glu-Abu | 0.003 | 9/9** |

N = 9
*The number of panelists who judged that γ-Glu-Nva was rather preferred since it could enhance the flavor and taste of the solution of tomato catsup, without changing the balance between them.
**The result indicates that γ-Glu-Nva is rather preferred since it can enhance the flavor and taste of the solution of tomato catsup, without changing the balance between them, at a significant level of 1%.

The foregoing results clearly indicate that γ-Glu-Nva shows the following quite remarkable effect: it can "enhance and make, more favorable, the tomato flavor and taste of, for instance, seasonings and sauces comprising tomato without changing the balance between them", when comparing them with those observed for γGlu peptides having high kokumi-imparting activities such as γ-Glu-Cys-Gly and γ-Glu-Abu, at concentrations capable of exhibiting the same kokumi-imparting activities. Tomato has widely been used in, for instance, seasonings, soup or broth, sauces and cooked and processed products. As has been discussed above, γ-Glu-Nva would permit the improvement of the flavor and taste of foods which make use of tomato, at a low cost, while using the same only in a trace amount and therefore, the use thereof is quite advantageous from the industrial standpoint.

While the invention has been described in detail with reference to preferred embodiments thereof, it will be apparent to one skilled in the art that various changes can be made, an equivalents employed, without departing from the scope of the invention. Each of the aforementioned documents is incorporated by reference herein in its entirety.

What is claimed is:

1. A method for imparting kokumi to a food or beverage composition comprising adding a dipeptide with the sequence of γ-Glu-Nva to said composition.

2. A method for preparing a food or beverage, or an intermediate used for preparing a food or beverage comprising the steps of:
   A) adding a flavor enhancer comprising a dipeptide with the sequence of γ-Glu-Nva to food ingredients,
   B) mixing them together; and
   C) optionally cooking the resulting mixture.

3. The method for preparing a food or beverage, or an intermediate used for preparing a food or beverage as set forth in claim 2, wherein said adding the flavor enhancer comprising a dipeptide with the sequence of γ-Glu-Nva to food ingredients comprises controlling the concentration of γ-Glu-Nva in the intermediate used for preparing a food or beverage to a level ranging from 0.005 to 600,000 ppm by mass.

4. The method for preparing a food or beverage as set forth in claim 3, wherein the method further comprises the step of adding an intermediate for preparing a food or beverage to other food ingredients while controlling the concentration of a dipeptide with the sequence of γ-Glu-Nva in the resulting food or beverage to a level ranging from 0.005 to 30 ppm by mass.

5. The method for preparing a food or beverage as set forth in claim 3, wherein said adding the flavor enhancer comprising a dipeptide with the sequence of γ-Glu-Nva to the food ingredients, and said mixing them together, comprises the step of controlling the concentration of γ-Glu-Nva in the resulting food or beverage to a level of from 0.005 to 30 ppm by mass.

6. The method for preparing a food or beverage as set forth in claim 2, wherein the food or beverage is a food comprising an herb and/or spice derived from a plant belonging to Labiatae.

7. The method for preparing a food or beverage as set forth in claim 2, wherein the food or beverage comprising miso.

8. The method for preparing a food or beverage as set forth in claim 2, wherein the food or beverage comprises tomato.

9. A method for enhancing the flavor and/or taste of a food or beverage, comprising the step of adding a composition comprising a dipeptide with the sequence of γ-Glu-Nva to a food or beverage.

10. The method as set forth in claim 9, wherein the flavor and/or taste-enhancing step is a kokumi-imparting step.

* * * * *